(12) United States Patent
Moll et al.

(10) Patent No.: US 8,498,691 B2
(45) Date of Patent: *Jul. 30, 2013

(54) ROBOTIC CATHETER SYSTEM AND METHODS

(75) Inventors: Frederic H. Moll, San Francisco, CA (US); Christopher R. Carlson, Menlo Park, CA (US); Federico Barbagli, San Francisco, CA (US); Daniel T. Wallace, Santa Cruz, CA (US); David Lundmark, Los Altos, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1499 days.

This patent is subject to a terminal disclaimer.

(21) Appl. No.: 11/640,099

(22) Filed: Dec. 14, 2006

(65) Prior Publication Data

US 2007/0156123 A1  Jul. 5, 2007

Related U.S. Application Data

(63) Continuation-in-part of application No. 11/637,951, filed on Dec. 11, 2006, now Pat. No. 8,190,238.

(60) Provisional application No. 60/750,590, filed on Dec. 14, 2005, provisional application No. 60/756,136, filed on Jan. 3, 2006, provisional application No. 60/749,369, filed on Dec. 9, 2005.

(51) Int. Cl.
*A61B 5/00* (2006.01)

(52) U.S. Cl.
USPC ........... 600/424; 600/411; 600/417; 600/427; 600/429; 700/245; 606/130; 715/700; 715/702; 623/2.11

(58) Field of Classification Search
USPC ................. 600/407, 424, 425, 114, 117, 118, 600/173; 606/130; 700/245; 715/702
See application file for complete search history.

(56) References Cited

U.S. PATENT DOCUMENTS

| | | | |
|---|---|---|---|
| 6,741,883 B2 * | 5/2004 | Gildenberg | 600/429 |
| 7,540,866 B2 * | 6/2009 | Viswanathan et al. | 606/1 |

(Continued)

FOREIGN PATENT DOCUMENTS

WO  2005087128  9/2005

OTHER PUBLICATIONS

PCT International Search Report for PCT/US2006/048058, Applicant: Hansen Medical, Inc., Forms PCT/ISA1210 and 220, dated Jun. 12, 2007 (6 pages).

(Continued)

*Primary Examiner* — Unsu Jung
*Assistant Examiner* — Amanda Lauritzen
(74) *Attorney, Agent, or Firm* — Vista IP Law Group LLP

(57) ABSTRACT

A robotically controlled guide instrument system, comprising an elongate flexible guide instrument; a drive assembly coupled to a proximal portion of the guide instrument and configured to maneuver a distal portion of the guide instrument; a master controller including a user interface that may be manipulated to actuate the drive assembly and thereby maneuver the distal portion the guide instrument; and a closure device detachably coupled to a delivery member carried by the guide instrument, the guide instrument maneuverable to position the closure device proximate an opening of a left atrial appendage of a person's heart such that the prosthesis may be detached from the delivery member and implanted to substantially close off the left atrial appendage.

16 Claims, 20 Drawing Sheets

U.S. PATENT DOCUMENTS

| | | | |
|---|---|---|---|
| 8,219,178 B2 * | 7/2012 | Smith et al. | 600/424 |
| 2002/0087049 A1 | 7/2002 | Brock | |
| 2003/0181942 A1 | 9/2003 | Sutton | |
| 2003/0199923 A1 | 10/2003 | Khairkhahan | |
| 2004/0034282 A1 * | 2/2004 | Quaid, III | 600/300 |
| 2004/0152972 A1 * | 8/2004 | Hunter | 600/424 |
| 2004/0171929 A1 * | 9/2004 | Leitner et al. | 600/424 |
| 2005/0027397 A1 * | 2/2005 | Niemeyer | 700/245 |
| 2005/0065589 A1 | 3/2005 | Schneider | |
| 2006/0025679 A1 * | 2/2006 | Viswanathan et al. | 600/424 |

OTHER PUBLICATIONS

PCT Written Opinion of the International Searching Authority for PCT/US2006/048058, Applicant: Hansen Medical, Inc., Form PCT1ISA1237, dated Jun. 12, 2007 (5 pages).

* cited by examiner

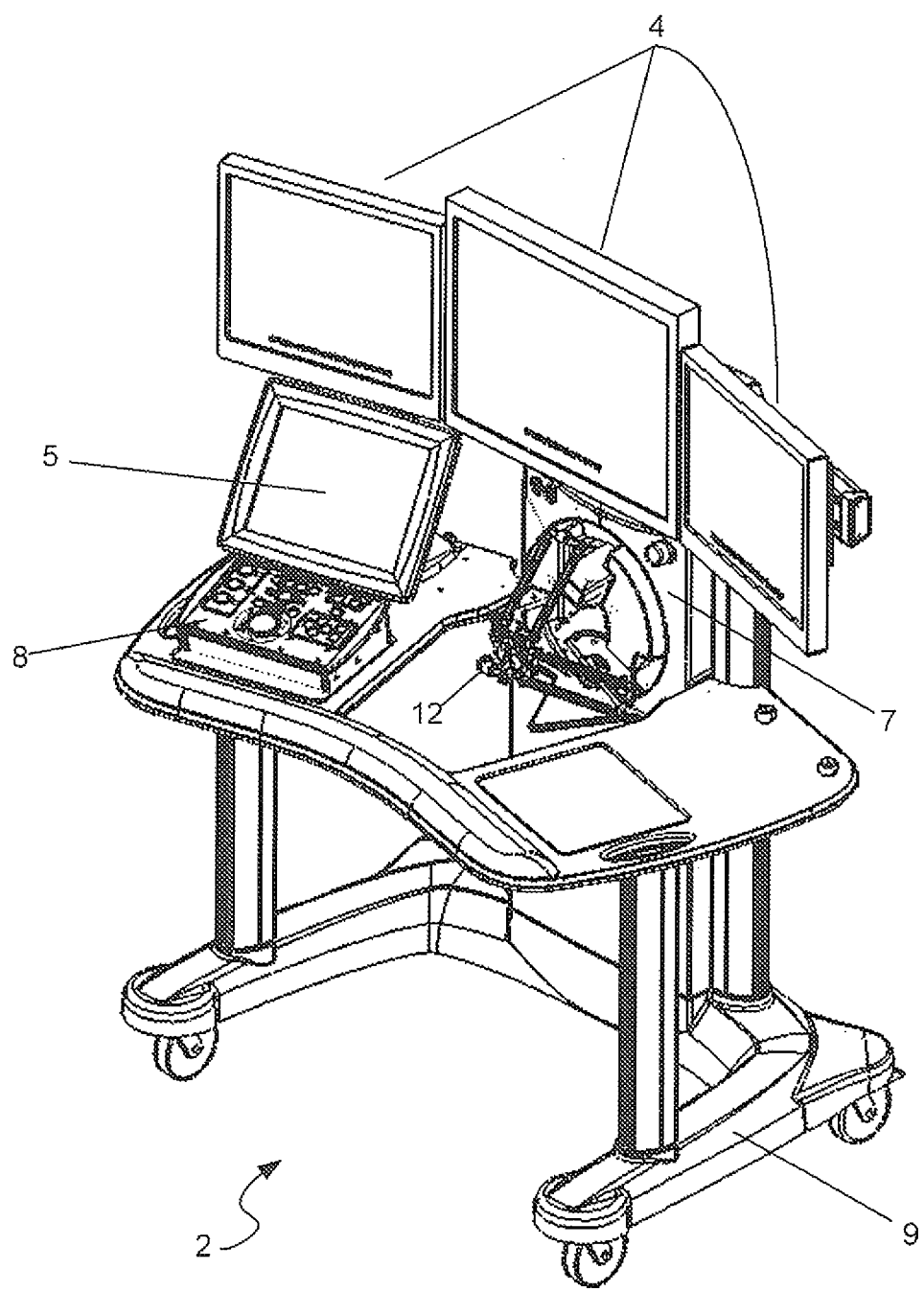
Fig 2.1

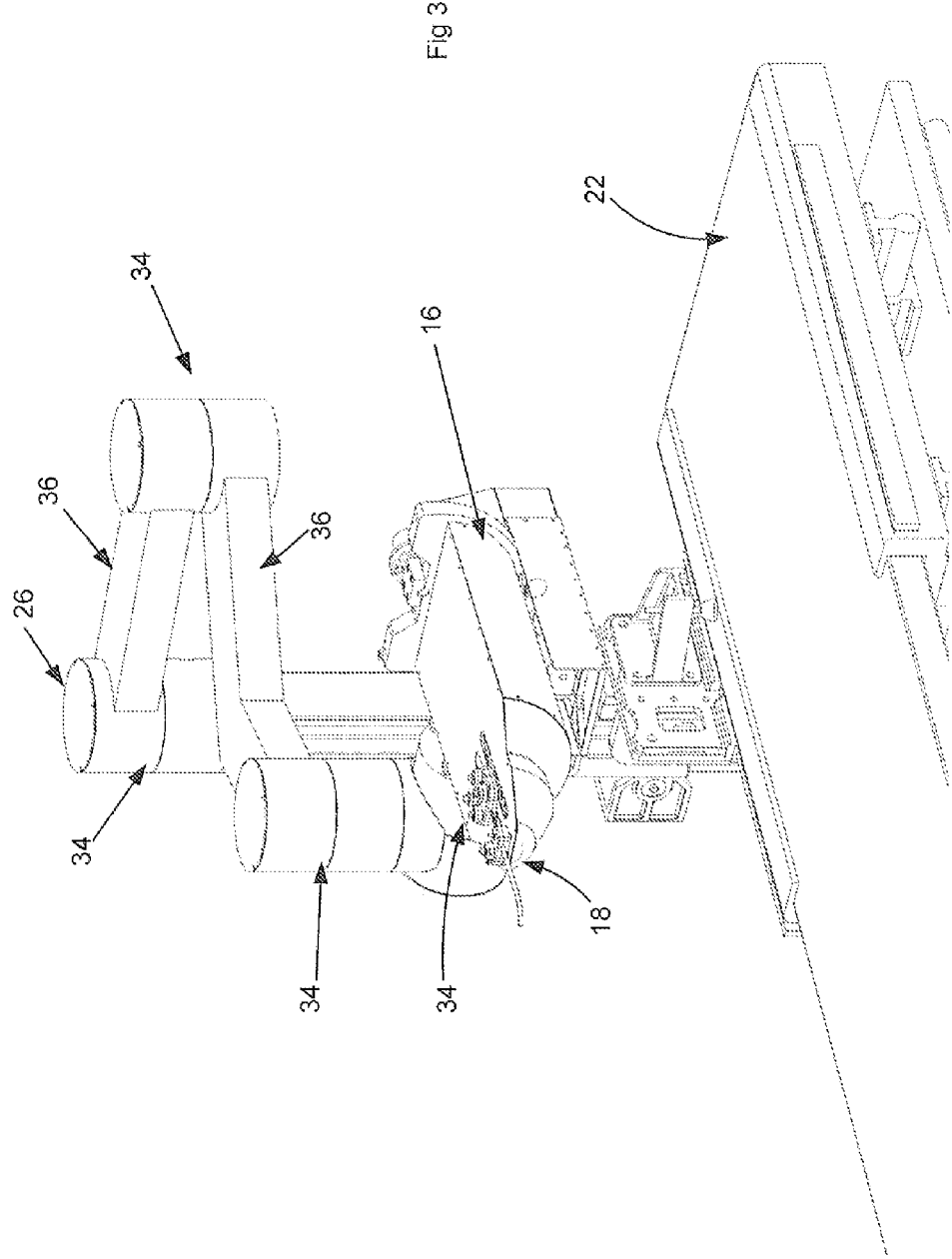

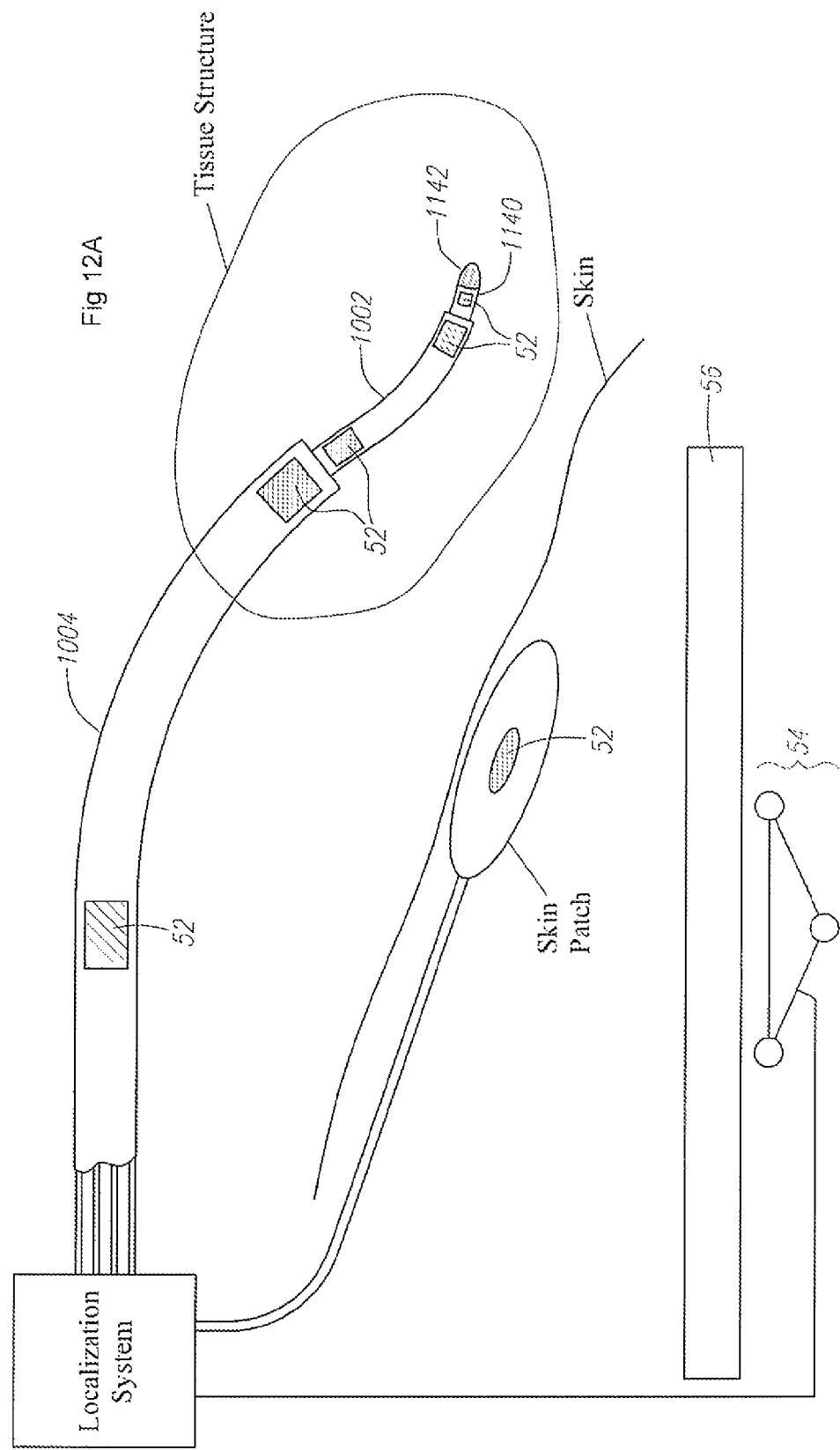

ROBOTIC CATHETER SYSTEM AND METHODS

RELATED APPLICATION DATA

The present application claims the benefit under 35 U.S.C. §119 to U.S. Provisional Patent Application Ser. Nos. 60/750,590, filed on Dec. 14, 2005, and 60/756,136, filed on Jan. 3, 2006. The foregoing applications are each incorporated by reference into the present application in their entirety for all purposes.

FIELD OF INVENTION

The invention relates generally to robotically controlled systems, such as telerobotic surgical systems, and more particularly to a robotic catheter system for performing minimally invasive diagnostic and therapeutic procedures.

BACKGROUND

Robotic interventional systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels or other lumens, via surgically-created wounds of minimized size, or both.

SUMMARY OF THE INVENTION

A robotically controlled guide instrument system comprises an elongate flexible guide instrument, a drive assembly coupled to a proximal portion of the guide instrument and configured to maneuver a distal portion of the guide instrument, and a master controller including a user interface that may be manipulated to actuate the drive assembly and thereby maneuver the distal portion the guide instrument.

In one embodiment, the system further comprises an occlusive prosthesis detachably coupled to an elongate delivery member carried by the guide instrument, wherein the guide instrument is maneuverable to position the occlusive prosthesis into a left atrial appendage of a person's heart such that the prosthesis may be detached from the delivery member and implanted into the left atrial appendage. The occlusive prosthesis may be self expanding, having a collapsed delivery configuration wherein carried in the guide instrument, and an expanded deployed configuration when deployed from the guide instrument into the left atrial appendage. The occlusive prosthesis may alternately be configured to be manually expanded once deployed from the guide instrument into the left atrial appendage.

In one embodiment, the system further comprises a closure device detachably coupled to a delivery member carried by the guide instrument, wherein the guide instrument is maneuverable to position the closure device proximate an opening of a left atrial appendage of a person's heart such that the prosthesis may be detached from the delivery member and implanted to substantially close off the left atrial appendage. The closure device may be self expanding, having a collapsed delivery configuration wherein carried in the guide instrument, and an expanded deployed configuration when deployed from the guide instrument across an opening of the left atrial appendage. By way of example, the closure device may comprise a plurality of tissue engaging members configured to engage tissue surrounding the opening of the left atrial appendage.

In one embodiment, the closure device comprises a clip. In one embodiment, the clip comprises a pair of opposing tissue engaging ends, each configured to engage tissue proximate an opening of the left atrial appendage. The delivery member may comprise a clip applier configured to crimp the clip after it has been deployed into tissue. By way of example, in one embodiment, the delivery member comprises a cinch member.

BRIEF DESCRIPTION OF THE DRAWINGS

The drawings illustrate the design and utility of illustrated embodiments of the invention, in which similar elements are referred to by common reference numerals, and in which:

FIG. 2.1 illustrates the operator control station of one embodiment.

FIG. 3 illustrates a closer view of a support assembly.

FIG. 12A illustrates one embodiment of a catheter instrument configuration comprising one or more localization sensors;

DETAILED DESCRIPTION

Figure 1:
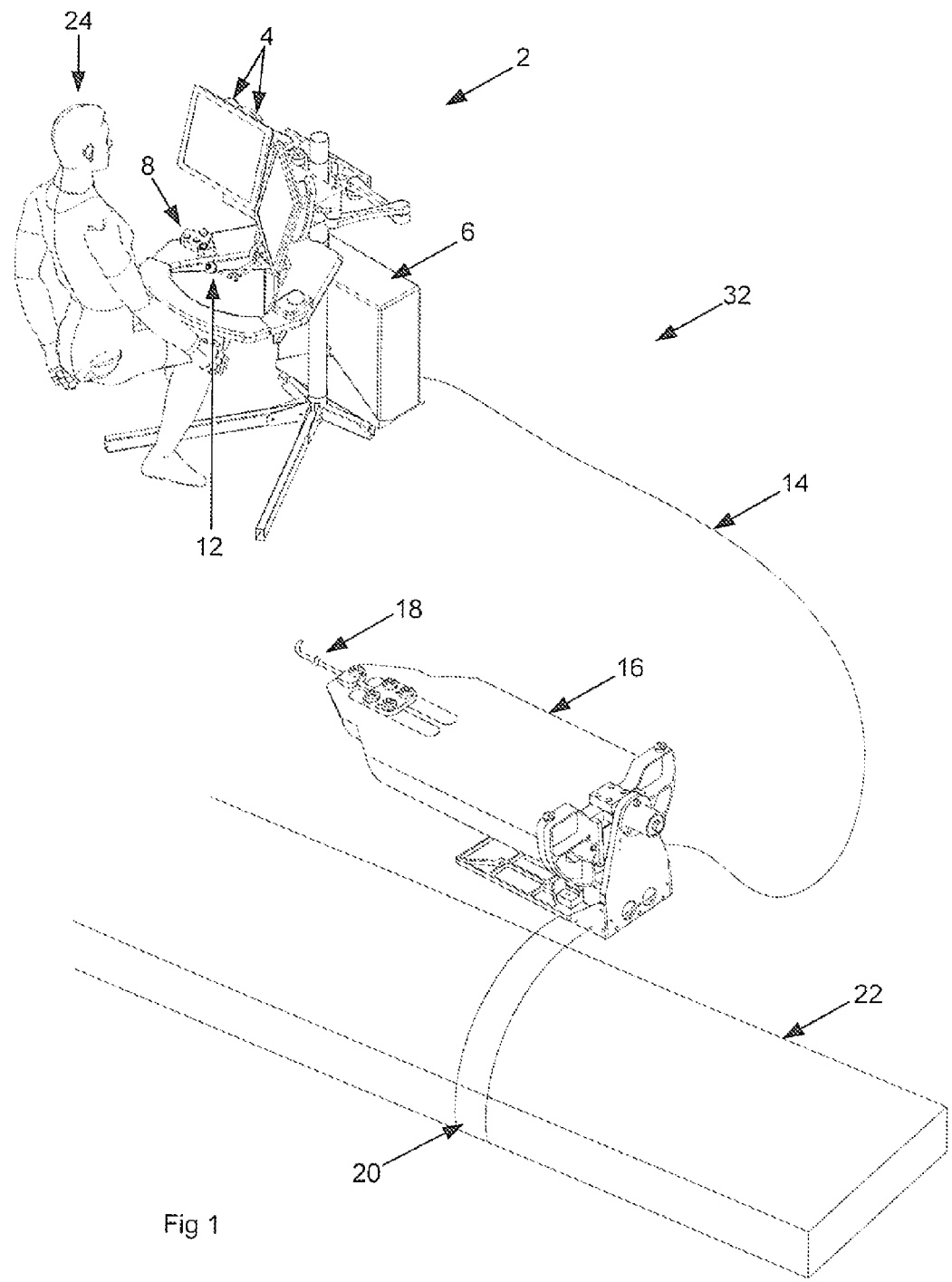
FIG. 1 illustrates one embodiment of a robotic catheter system.

Referring to FIG. 1, one embodiment of a robotic catheter system (32), includes an operator control station (2) located remotely from an operating table (22), to which a instrument driver (16) and instrument (18) are coupled by a instrument driver mounting brace (20). A communication link (14) transfers signals between the operator control station (2) and instrument driver (16). The instrument driver mounting brace (20) of the depicted embodiment is a relatively simple, arcuate-shaped structural member configured to position the instrument driver (16) above a patient (not shown) lying on the table (22).

Figure 2:
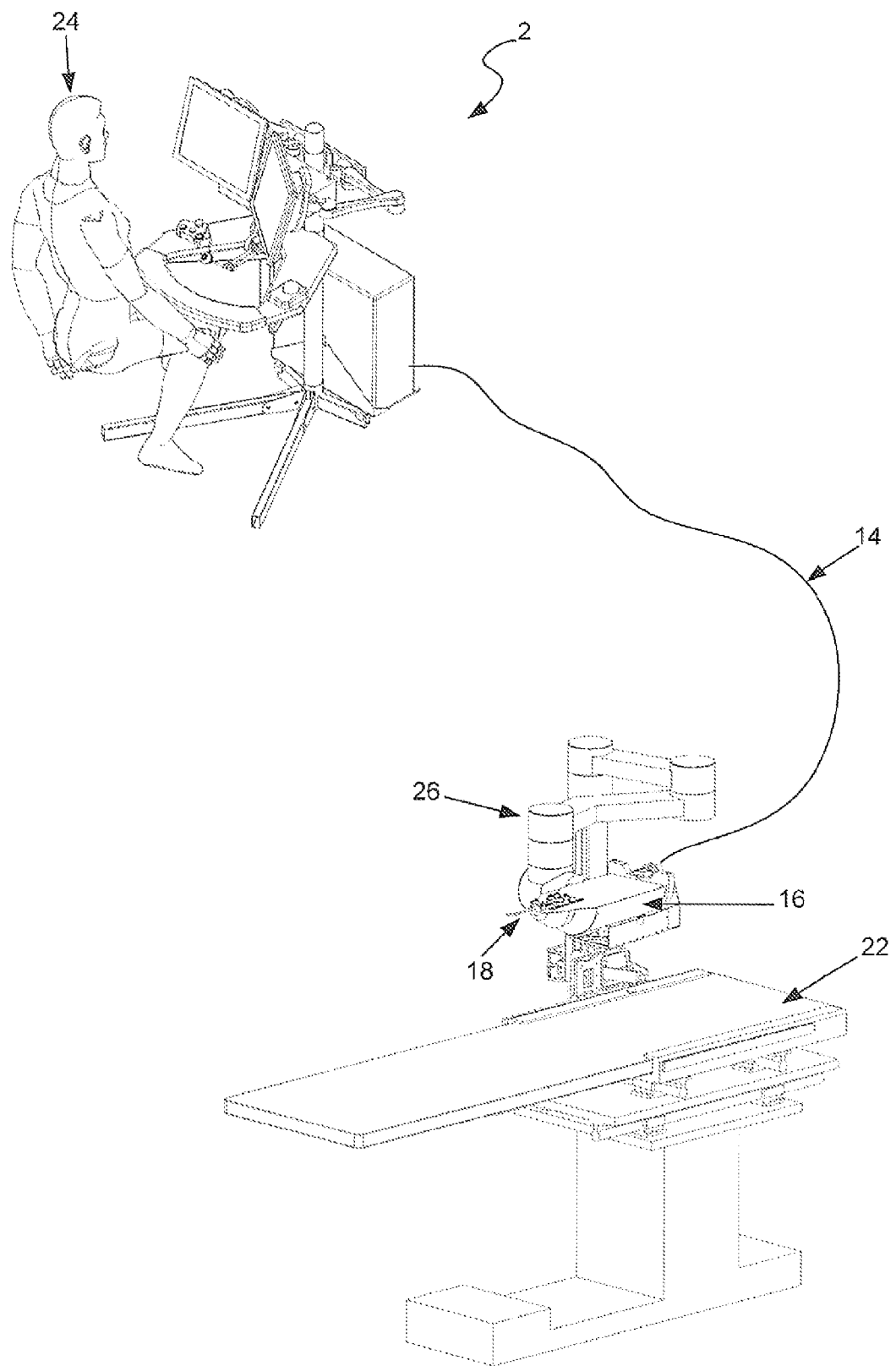
FIG. 2 illustrates another embodiment of a robotic catheter system.

In FIG. 2, another embodiment of a robotic catheter system is depicted, wherein the arcuate-shaped member (20) is replaced by a movable support-arm assembly (26). The support assembly (26) is configured to movably support the instrument driver (16) above the operating table (22) in order to position the instrument driver (16) for convenient access into desired locations relative to a patient (not shown). The support assembly (26) in FIG. 2 is also configured to lock the instrument driver 16 into position once it is positioned.

Referring to FIG. 2.1, a view of another variation of an operator control station (2) is depicted having three displays (4), a touchscreen user interface (5), and a control button console (8). The master input device (12) depicted in the embodiment of FIG. 2.1 is depicted and described in further detail in U.S. application Ser. No. 11/637,951 (FIG. 105B) which is incorporated by reference herein. Also depicted in the embodiment of FIG. 2.1 is a device disabling switch (7) configured to disable activity of the instrument temporarily. The cart (9) depicted in FIG. 2.1 is configured for easy movability within the operating room or catheter lab, one advantage of which is location of the operator control station (2) away from radiation sources, thereby decreasing radiation dosage to the operator. FIG. 2.2 depicts a reverse view of the embodiment depicted in FIG. 2.1

FIG. 3 provides a closer view of the support assembly (26) depicted in the embodiment of FIG. 2.1. The support assembly (26) comprises a series of rigid links (36) coupled by electronically braked joints (34). The joints (34) allow motion of the links (36) when energized by a control system (not shown), but otherwise prevent motion of the links. The control system may be activated by a switch (e.g., a footswitch or thumb switch), or computer interface. In another embodiment, the rigid links (36) may be coupled by mechanically lockable joints, which may be locked and unlocked manually using, for example, locking pins, screws, or clamps. The rigid links (36) preferably comprise a light but strong material, such as high-gage aluminum, shaped to withstand the stresses and strains associated with precisely maintaining a three-dimensional position of the approximately ten pound weight of a typical embodiment of the instrument driver (16) once the position of the link (36) is fixed.

In summary, a support assembly (26), or support structure, is configured to allow for easy repositioning of an instrument driver or other device relative to an operating table when an actuation button is depressed, thereby activating a solenoid and releasing two electronic brakes. The position of an instrument driver then may be easily fine-tuned, for example, or modified quickly and substantially to remove the instrument driver from the immediate area of a patient on an operating table for quick medical intervention with broad physical access. Constraints limit the movement of the instrument driver relative to the operating table—i.e., a pan-rotate interface (13), a horizontal extension member (15) with a rotational position maintaining timing chain (73) for distally-coupled structures, and brake-lockable rotations about two axes of rotation (125, 119) which may be parallel and both perpendicular relative to the plane of the operating table—to provide desirable mechanics. When an actuation button is not depressed and the structures are substantially locked into position relative to each other, with the exception of manually-activated lead screw pitch adjustment of an instrument driver interface (21), the support assembly (26) is configured to provide a robust structural platform upon which an instrument driver or other device may be positioned relative to an operating table.

Figure 4:
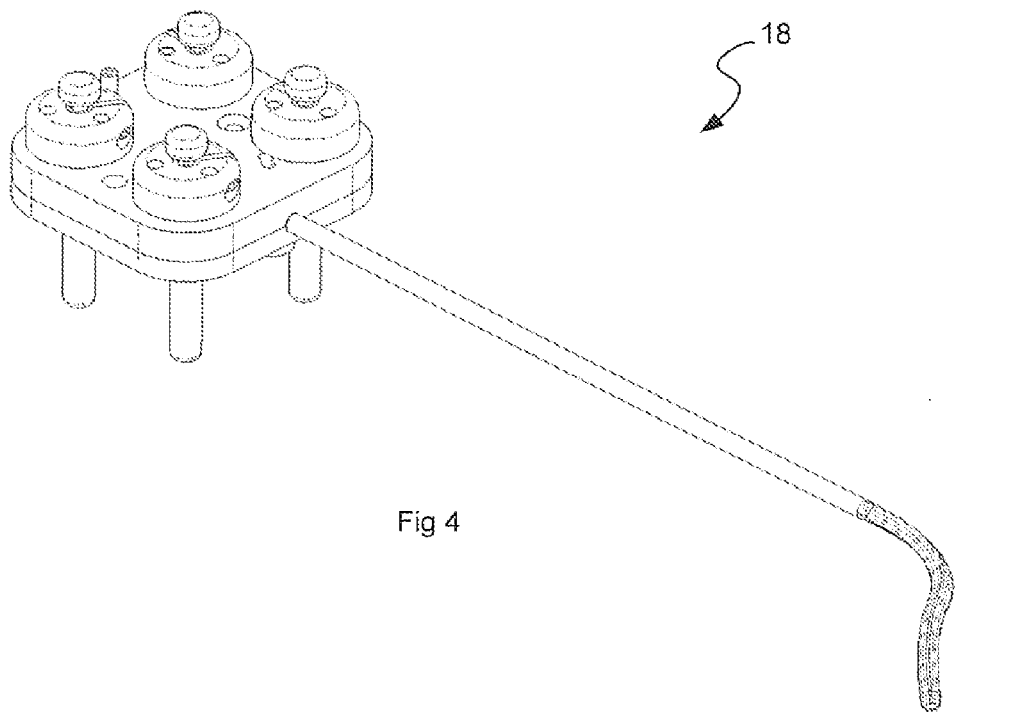
FIG. 4 illustrates an isometric view of an instrument for use with one embodiment of an instrument driver.
Figure 5:
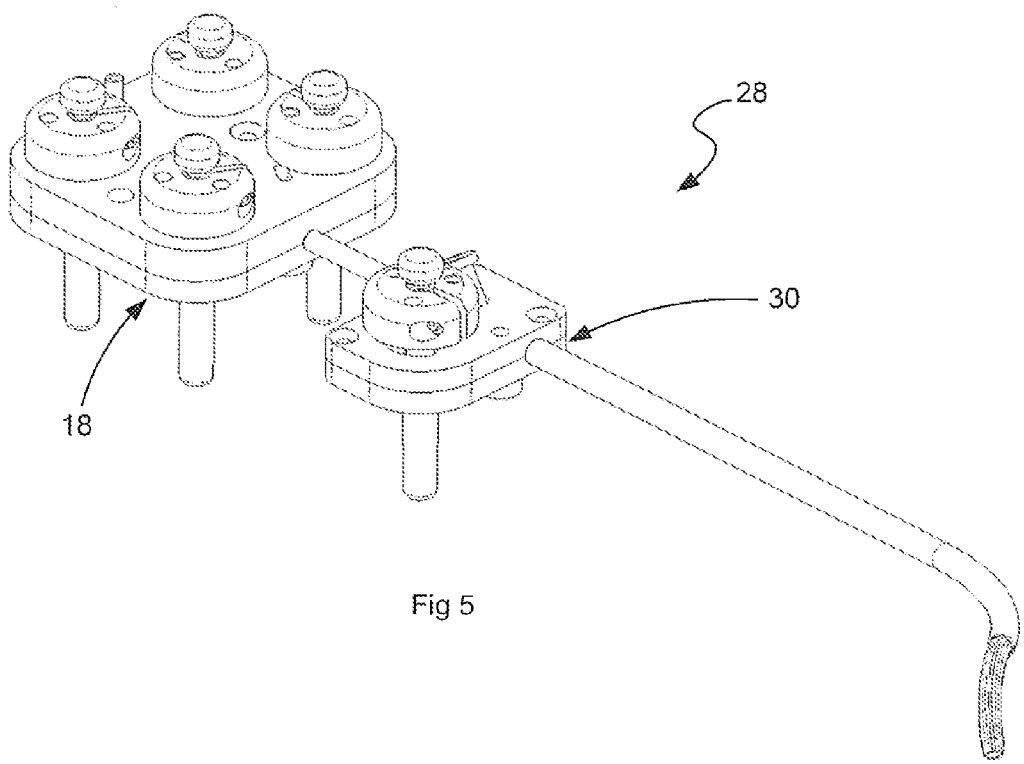
FIG. 5 illustrates an isometric view of two instruments arranged in a co-axial relationship for use with another embodiment of an instrument driver.

FIGS. 4 and 5 depict isometric views of respective embodiments of instruments configured for use with an embodiment of the instrument driver (16), such as that depicted in FIGS. 1-3. FIG. 4 depicts an instrument (18) embodiment without an associated coaxial sheath coupled at its midsection. FIG. 5 depicts a set of two instruments (28), combining an embodiment like that of FIG. 4 with a coaxially coupled and independently controllable sheath instrument (30). To distinguish the non-sheath instrument (18) from the sheath instrument (30) in the context of this disclosure, the "non-sheath" instrument may also be termed the "guide" instrument (18).

Figure 6:
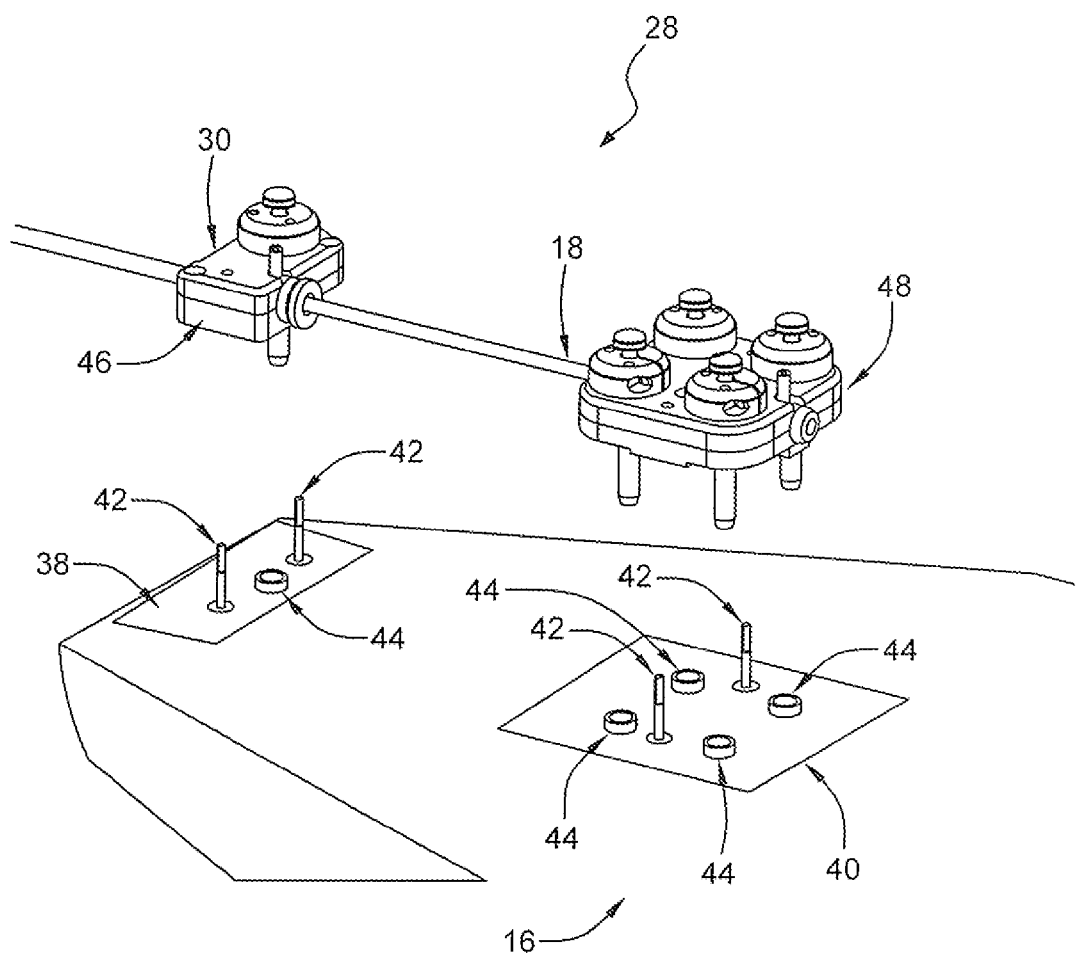
FIG. 6 illustrates an exemplary scheme for mounting a coaxial instrument pair on a instrument driver.

Referring to FIG. 6, a set of instruments (28), such as those in FIG. 5, is depicted adjacent an instrument driver (16) to illustrate an exemplary mounting scheme. The sheath instrument (30) may be coupled to the depicted instrument driver (16) at a sheath instrument interface surface (38) having two mounting pins (42) and one interface socket (44) by sliding the sheath instrument base (46) over the pins (42). Similarly, and preferably simultaneously, the guide instrument base (48) may be positioned upon the guide instrument interface surface (40) by aligning the two mounting pins (42) with alignment holes in the guide instrument base (48). As will be appreciated, further steps may be required to lock the instruments (18, 30) into place upon the instrument driver (16). By way of example, in one embodiment, the instruments (18, 30) are provided for a medical procedure in sterile packaging, while the instrument driver (16) is not necessarily sterile. In accordance with conventional sterile medical procedure, the non-sterile instrument driver (16) is preferably isolated from the patient by a sterile barrier of some type.

Various and alternative embodiments of the foregoing robotic catheter system, including embodiments of their component parts, sub-parts, assemblies, and sub-assemblies are disclosed and described in great detail, along with various and multiple examples of diagnostic and therapeutic procedures being performed by embodiments of the foregoing, in the above-incorporated U.S. patent application Ser. No. 11/637, 951.

Referring to FIGS. 7A-10F, the above-described and referenced robotic catheter system may be utilized to accurately position and deploy various intra-body implants and prostheses, such as those configured for deployment within the left atrial appendage ("LAA") of a patient's heart.

Figure 7A:
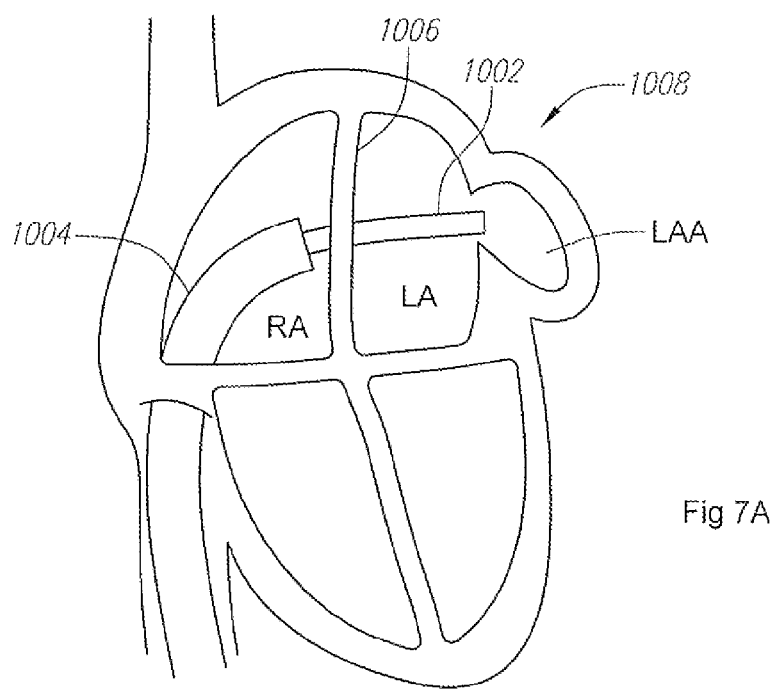
FIG. 7A illustrates one embodiment of a method and apparatus wherein a robotic guide instrument coaxially positioned within a robotic sheath and navigated across the atrial septum of a patient's heart.
Figure 7B:
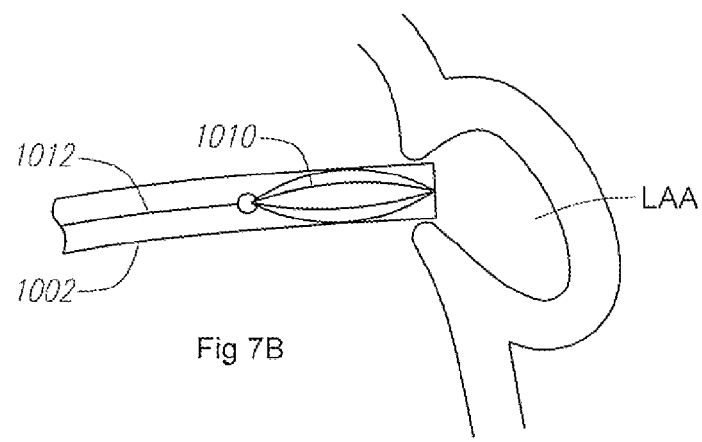
FIG. 7B illustrates one embodiment of a method and apparatus wherein a prosthesis is advanced on a delivery member through a robotic guide instrument into the left atrial appendage.
Figure 7C:
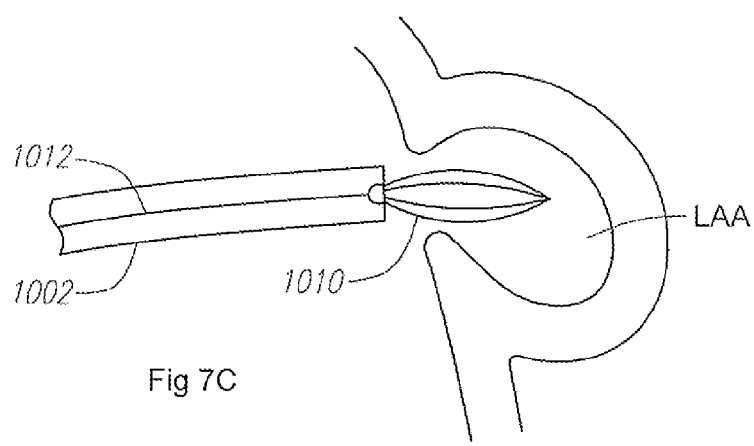
FIGS. 7C-D illustrate the expansion of the prosthesis of FIG. 7B in the left atrial appendage.
Figure 7D:
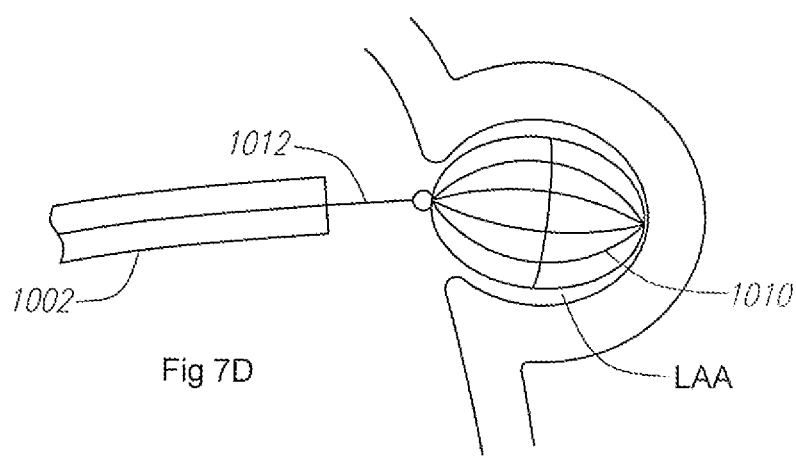
Figure 7E:
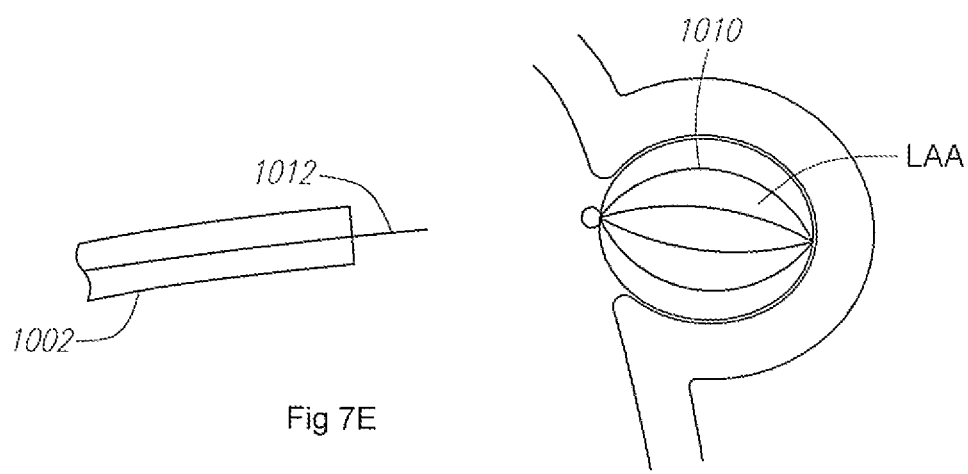
FIG. 7E illustrates the detaching of the prosthesis of FIG. 7B from the delivery member.
Figure 7F:
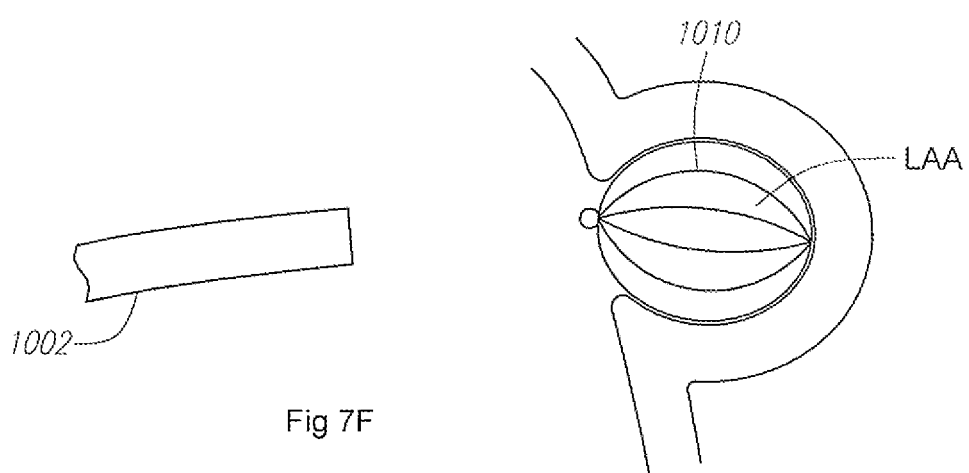
FIG. 7F illustrates the withdrawing of the delivery member into the guide instrument, and the guide instrument, in turn, withdrawing from the left atrium.

Referring to FIG. 7A, a robotic guide instrument 1002 coaxially positioned within a robotic sheath 1004 may be extended form the sheath 1004 and navigated across the atrial septum 1006 of a patient's heart 1008, as is disclosed and described in the above-incorporated U.S. patent application Ser. No. 11/637,951, in order to access the LAA. As seen in FIG. 7B, a prosthesis 1010, such as ones available from Atritech, Inc., is advanced on a delivery member 1012 through the robotic guide instrument 1002, into the LAA, where it is pushed out of the distal end opening of the guide instrument 1002 and allowed to expand (in the case of a self-expanding prosthesis 1010), or is otherwise mechanically expanded, in the LAA (shown in FIGS. 7C and 7D). Subsequently, the guide instrument 1002 is withdrawn from the LAA (shown in FIG. 7D), and the prosthesis 1010 is detached from the delivery member 1012 (shown in FIG. 7E), remaining implanted in (thereby occluding) the LAA. The delivery member 1012 is then withdrawn into the guide instrument 1002 (shown in FIGS. 7E and 7F), and the guide instrument 1002, in turn, may be withdrawn from the left atrium (LA), and from being deployed across the atrial septum 1006, and into the sheath 1004.

It may be desirable to (optionally) suture, clip, or staple the mouth of the LAA after the prosthesis 1010 is detached and expanded therein, using a suture, clip, staple, or the like, that is delivered through the robotic guide instrument 1002. It may also be desirable to seal the surface over the LAA opening (i.e., across the prosthesis 1010) utilizing a surgical sealant, such as the product marketed by Baxter under the tradename CoSeal, deployed from the robotic guide instrument 1002 and/or use a conventional ablation catheter delivered through the robotic guide instrument 1002 to form one or more lesions over and around the closed LAA to form an appropriate mechanical and/or conductive block with RF energy, high-intensity focused ultrasound, low-temperature cryoablation, or the like.

Advantageously, a system according to one embodiment of the invention includes the robotic catheter system, including the guide instrument 1002 and (optionally) the robotic sheath 1004, along with the delivery member 1012 and detachable prosthesis implant 1010.

Figure 8A:
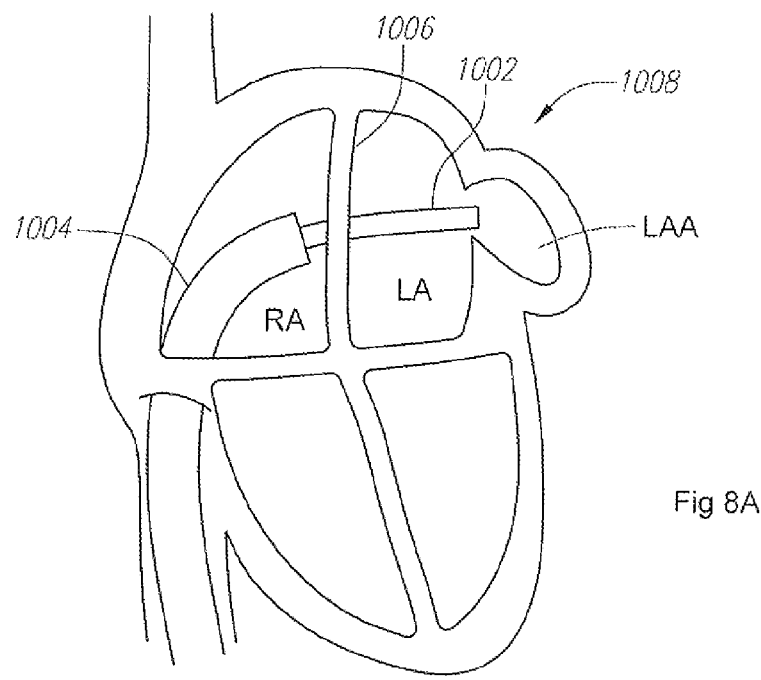
FIGS. 8A-F illustrate one embodiment of a method and apparatus for delivery of an implantable closure device through a robotic guide instrument on a delivery member into a left atrial appendage.
Figure 8B:
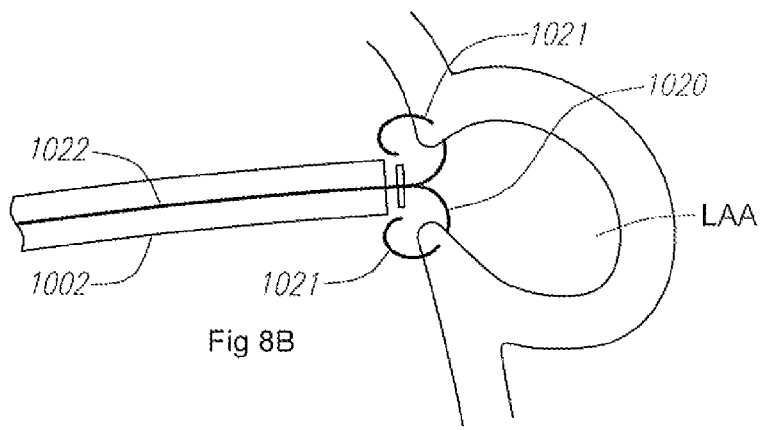
Figure 8C:
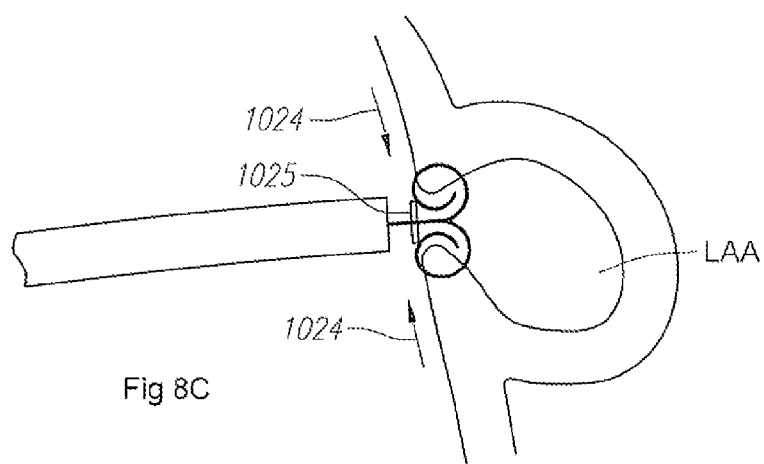
Figure 8D:
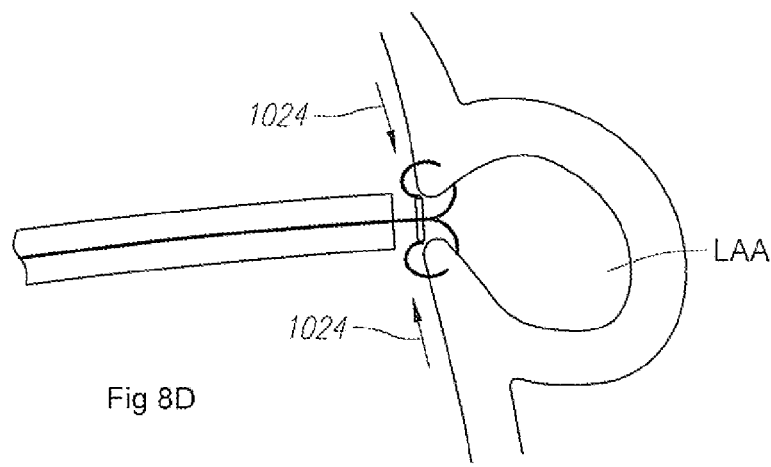
Figure 8E:
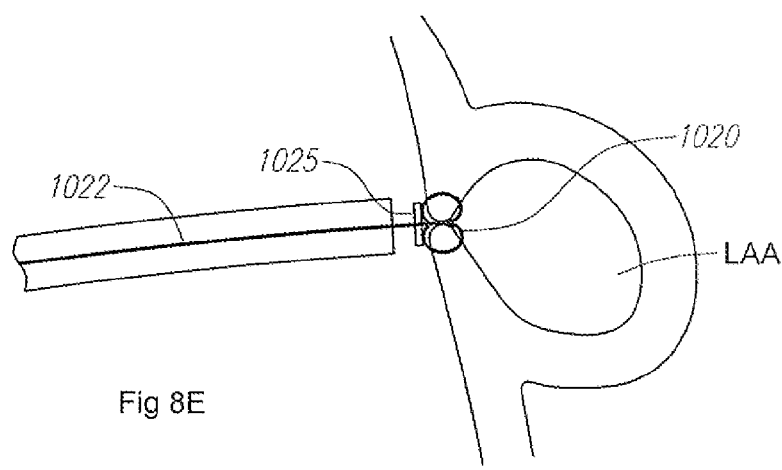
Figure 8F:
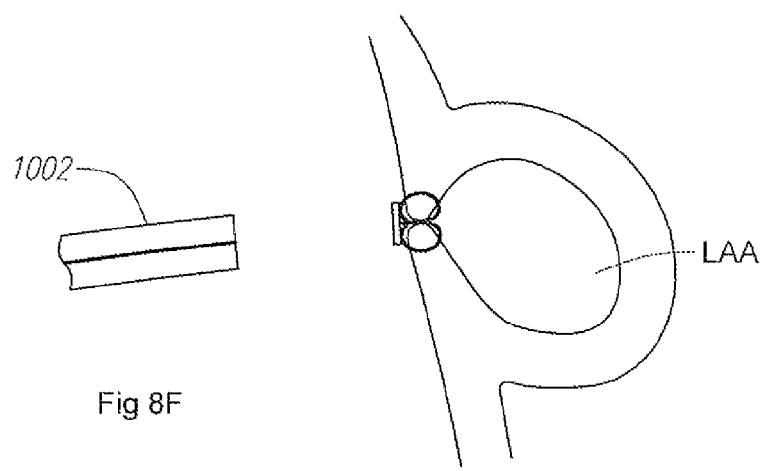

Referring to FIGS. 8A-8F, in another embodiment, an implantable closure device 1020, such as nitinol clips developed by Coalescent Surgical, now Medtronic, is delivered through the robotic guide instrument 1002 on a delivery member 1022 into LAA. The closure device 1020 self-expands when delivered out of the distal end opening of the robotic guide instrument 1002, as shown in FIG. 8B, and has tissue engaging ends 1021 that attach to the tissue area around the mouth of the LAA. Once the tissue engaging ends 1021 of the device 1020 engage the tissue around the LAA opening, the delivery member 1022 is pulled back into the robotic guide instrument 1002, thereby causing the tissue to be drawn together to close off the LAA, as indicated by the arrows 1024 in FIGS. 8C-D. A washer-like member 1025 may be used to help cinch together the tissue engaging ends 1021 of the device 1020 as the delivery member 1022 is withdrawn into the guide instrument 1002. Once the LAA is substantially closed off (as shown in FIG. 8E), the delivery member 1022 is detached from the device 1020 and withdrawn back into the robotic guide instrument 1002, which is then itself withdrawn from the area of the LAA (FIG. 8F).

Again, it may be desirable to (optionally) seal the surface over the LSS opening (i.e., across the closure device 1020) and/or use a conventional ablation catheter delivered through the robotic guide instrument 1002 to form one or more lesions over and around the closed LAA to form an appropriate conductive and/or mechanical block.

Advantageously, a system according to one embodiment of the invention includes the robotic catheter system, including the guide instrument 1002 and (optionally) the robotic sheath 1004, along with the delivery member 1022 and detachable closure device 1020.

Figure 9A:
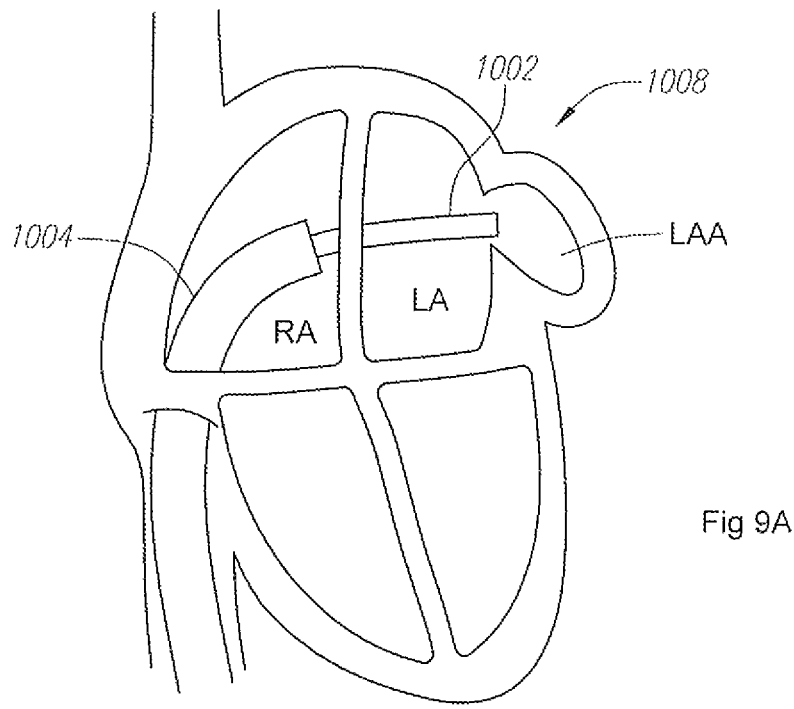
FIGS. 9A-D illustrate one embodiment of a method and apparatus for advancing a clip applier through a robotic guide instrument to deploy a clip directly into the tissue around the opening of a left atrial appendage.
Figure 9B:
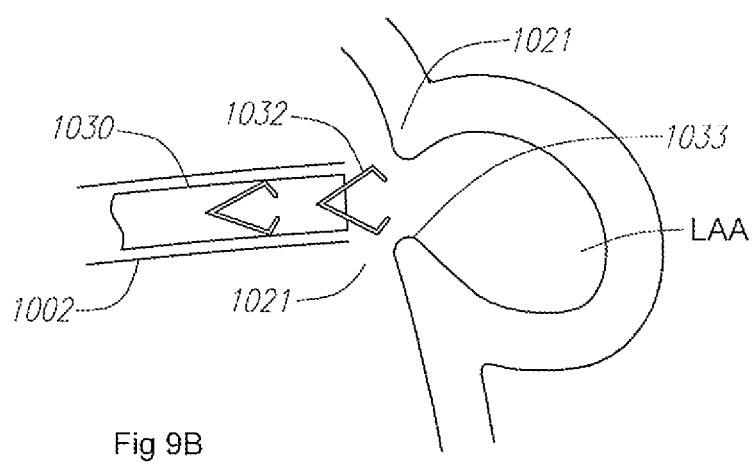
Figure 9C:
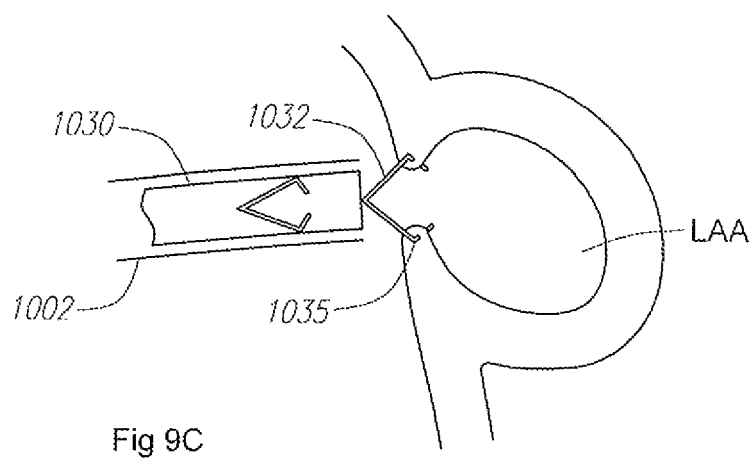
Figure 9D:
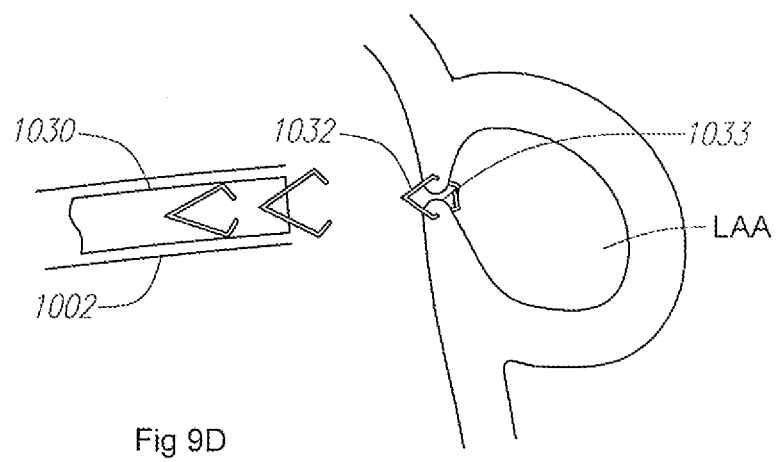

FIGS. 9A-D depict a clip applier 1030 being advanced through the robotic guide instrument 1002 to deploy a clip 1032 directly into the tissue 1033 around the opening of the LAA. As best seen in FIG. 9C, the clip has tissue engaging ends 1035 that pierce and engage the tissue 1033 around the LAA opening, after which the ends 1035 of the clip 1032 are crimped together by the clip applier 1030 to close off the LAA, as seen in FIG. 9D.

Figure 10A:
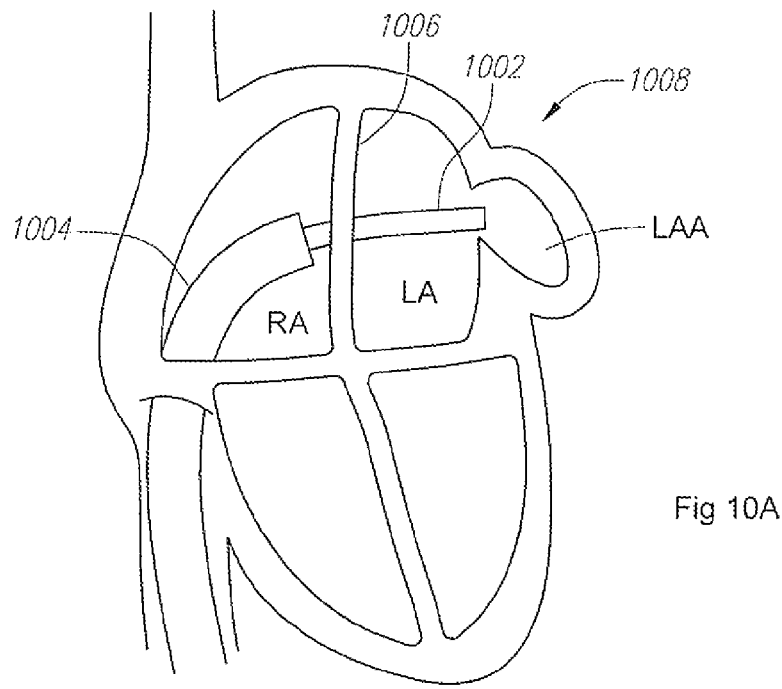
FIGS. 10A-F illustrate another embodiment of a method and apparatus utilizing a clip applier to close the opening of a left atrial appendage from a precision positioning platform, such as the subject robotic catheter guide instrument.
Figure 10B:
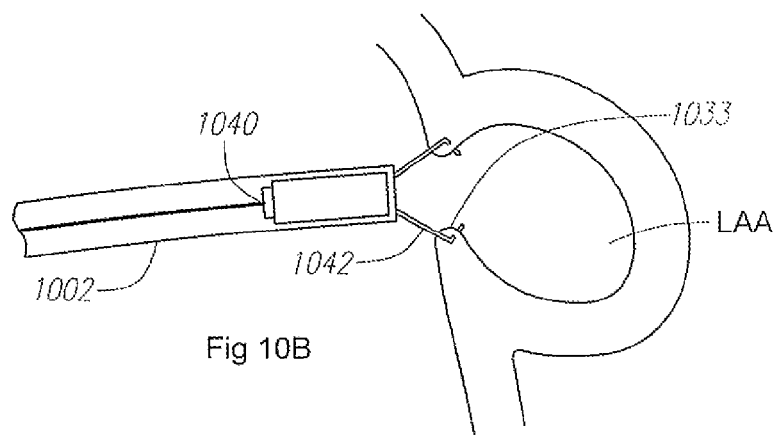
Figure 10C:
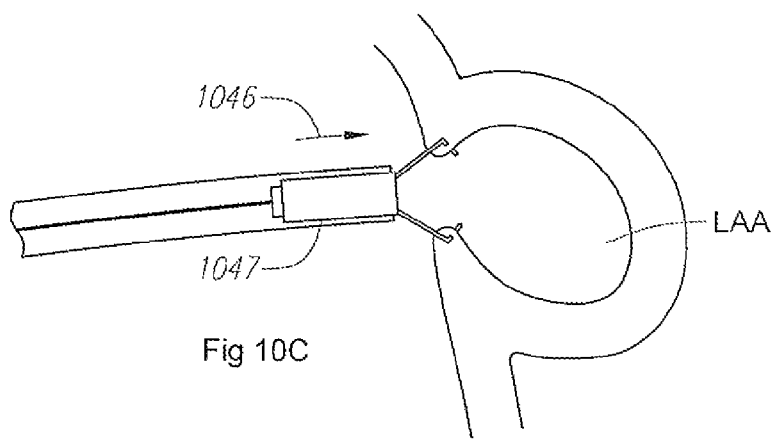
Figure 10D:
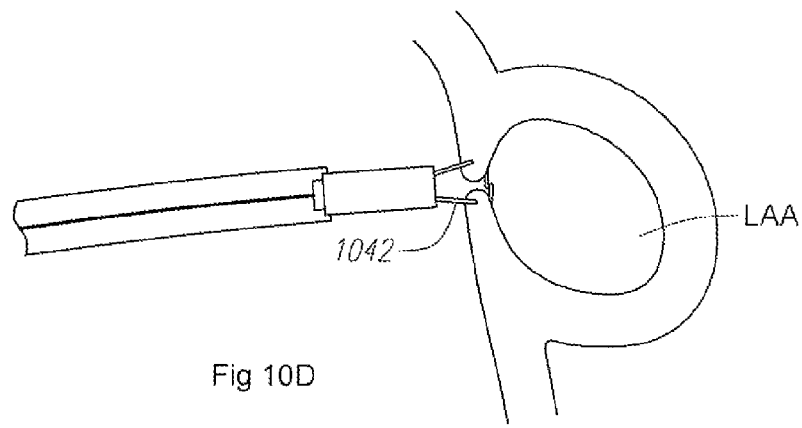
Figure 10E:
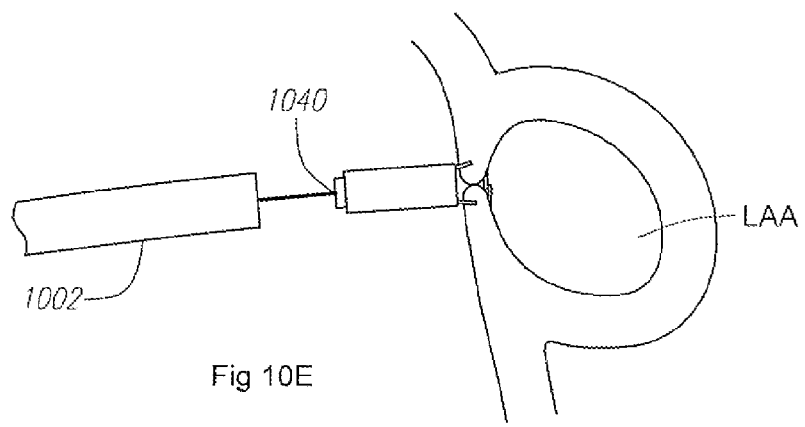
Figure 10F:
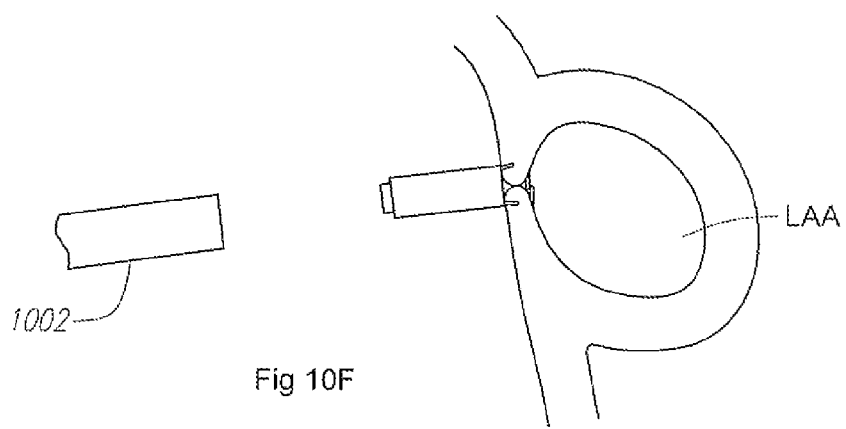

FIGS. 10A-F depict another variation of a clip applier 1040, which may be utilized to close the opening of a LAA from a precision positioning platform, such as the subject robotic catheter guide instrument 1002. In this embodiment, the clip applier 1040 includes a slidable cinch member 1047 that is moved distally relative to the distal end opening of the guide instrument 1002 (as seen in FIGS. 10C-E) to thereby crimp the ends of a clip that is embedded in the tissue 1033 around the opening of he LAA (as indicated by arrow 1046 in FIG. 10C). Once the LAA is substantially closed off (as shown in FIG. 10F), the clip applier 1040 is withdrawn back into the robotic guide instrument 1002, which is then itself withdrawn from the area of the LAA (FIG. 8F).

Once again, it may be desirable to seal the surface over the LAA opening (i.e., across the clips 1032, 1042) and/or use a conventional ablation catheter delivered through the robotic guide instrument 1002 to form one or more lesions over and around the closed LAA to form an appropriate conductive and/or mechanical block.

Advantageously, a system according to one embodiment of the invention includes the robotic catheter system, including the guide instrument 1002 and (optionally) the robotic sheath 1004, along with a clip applier (e.g., clip applier 1030 or clip applier 1040).

Figure 11A:
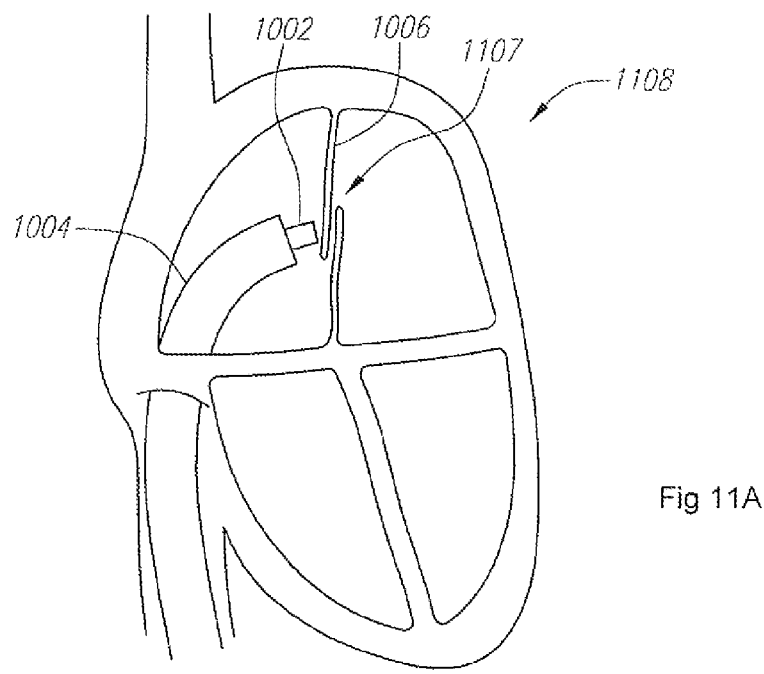
FIGS. 11A-G illustrate various embodiments of methods and apparatuses for closing an atrial septal defect with a distal end tool navigated and/or deployed with a robotic guide instrument.

Referring to FIGS. 11A-G, in accordance with a different aspect of the invention, an atrial septal defect, such as a patent fossa ovalis ("PFO") 1007 (i.e., an opening through the atrial septum wall 1006 in a person's heart 1008) may be closed using any one of a number of different distal end tools navigated and/or deployed with the subject robotic guide instrument 1002, which may optionally extend from a robotic sheath 1004. As seen in FIG. 11A, the PFO 1107 is approached in the left atrium (LA) with a coxial guide/sheath robotic instrument pair 1002/1004 operated by a robotic catheter system, as is disclosed and described in the above-incorporated U.S. patent application Ser. No. 11/637,951.

Figure 11B:
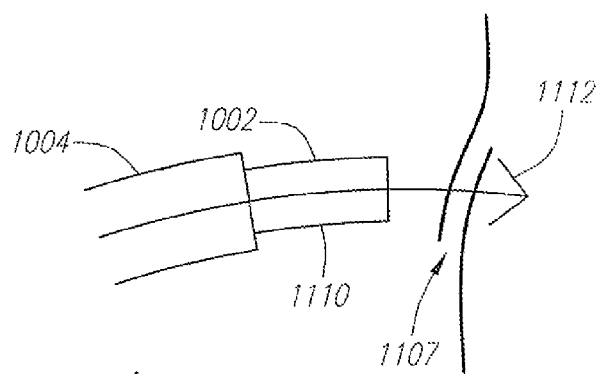
Figure 11C:
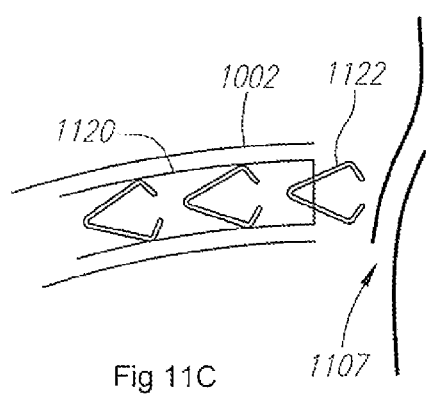
Figure 11D:
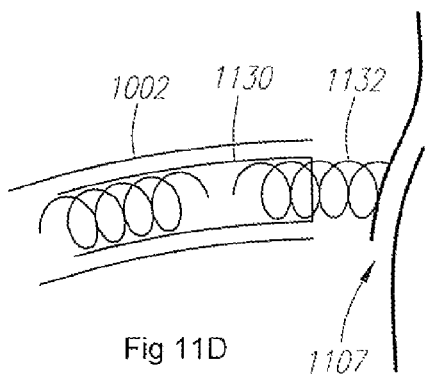

In the embodiment of FIG. 11B, once the distal end opening of the robotic guide instrument 1002 is positioned at the PFO 1107 (in one embodiment approximately orthogonal to the atrial wall 1106), a toggle-bolt type prosthesis 1112 deployed on a delivery member 1110 is utilized to pierce both sides of the PFO 1107 and bring them into coaptation for healing against each other. FIG. 11C depicts another embodiment, wherein a clip applier 1120 is deployed from the guide instrument 1002 and utilized to engage the two sides of the PFO 1107 using a clip 1122. FIG. 11D depicts another embodiment, in which one or more rotational tissue coaptation deployment members (i.e., small helical coils) 1132 are delivered from a deployment member 1130 carried in the guide instrument 1002, and rotated through the POF walls 1107, where they are left in place to engage the two sides of the PFO 1107 for healing.

Figure 11E:
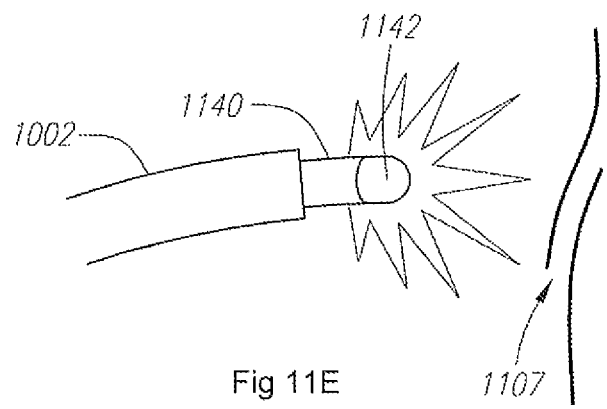

FIG. 11E depicts yet another embodiment, wherein RF energy is applied from an electrode 1142 on an ablation catheter 1140 carried in the guide instrument to the tissue area of the PFO 1107, thereby cause a healing response that will close the PFO 1107. A line or matrix of ablations may be preferred, and ablations may be created with means other than RF energy, for example including low-temperature cryoablation and/or high-intensity focused ultrasound ablation.

Figure 11F:
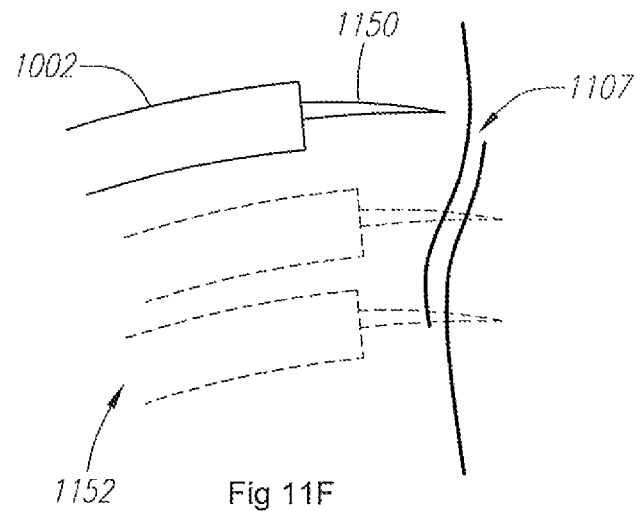
Figure 11G:
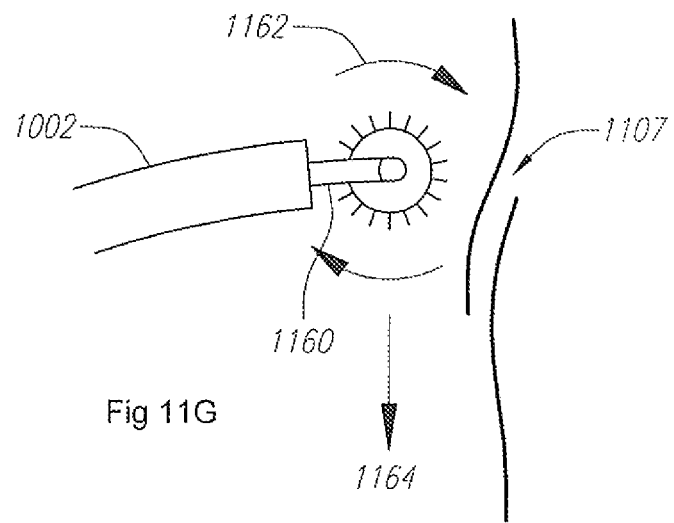

In another embodiment, puncturing or other mechanical irritation, as opposed to, or in addition to, the aforementioned techniques, may be utilized to stimulate a healing response and thereby cause closure of a PFO. For example, as depicted in FIG. 11F, a line or matrix of small punctures or irritations (line or matrix formation indicated by the phantom punctures 1152), or single puncture or irritation from a stylet 1150 extending from the guide instrument 1002 into the tissue walls around the PFO 1107 may be utilized to invoke a healing response to close the PFO. As shown in FIG. 11G, a rotatable or rotating irritation and/or puncture device such as a burr 1160 (rotation indicated be line 1162) or similar device distally deployed from the robotic guide instrument 1002 may be engaged to the tissue forming the PFO 1107 to cause inflammation sufficient to heal the PFO. Lateral movement of the burr 1160 across the PFO 1107 is indicated by line 1164.

Advantageously, a system according to one embodiment of the invention includes the robotic catheter system, including the guide instrument 1002 and (optionally) the robotic sheath 1004, along with any one or more of the toggle-bolt type prosthesis 1112 (and delivery member 1110), clip applier 1120 (and clips 1122), rotational tissue coaptation deployment members 1132 (and deployment member 1130), ablation catheter 1140, stylet 1150, and rotating burr 1150.

To facilitate instinctive operation of the system, it is preferable to have the master input device coordinate system at least approximately synchronized with the coordinate system of at least one of the two views. In other words, it is preferable for "instinctive" control and navigation that "up" on the master input device corresponds to "up" on at least one of the displayed views, and similarly, "left" corresponds to "left", etc. As is disclosed and described in the above-incorporated U.S. patent application Ser. No. 11/637,951, in various embodiments of the robotic catheter system, multiple displays preferably are provide to the system operator, the diplays depicting both real or near-real time image data acquired, for example, using ultrasound, fluoroscopy, and/or localization techniques.

Figure 12B:
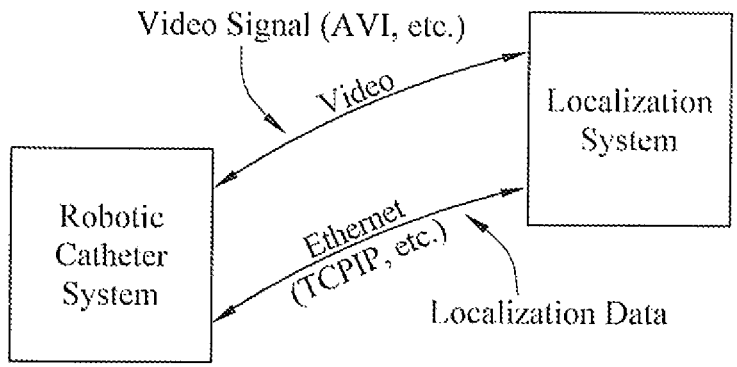
FIG. 12B is a block diagram illustrating one embodiment of a system wherein localization data is communicated between a robotic catheter system and a localization system.
Figure 13A:
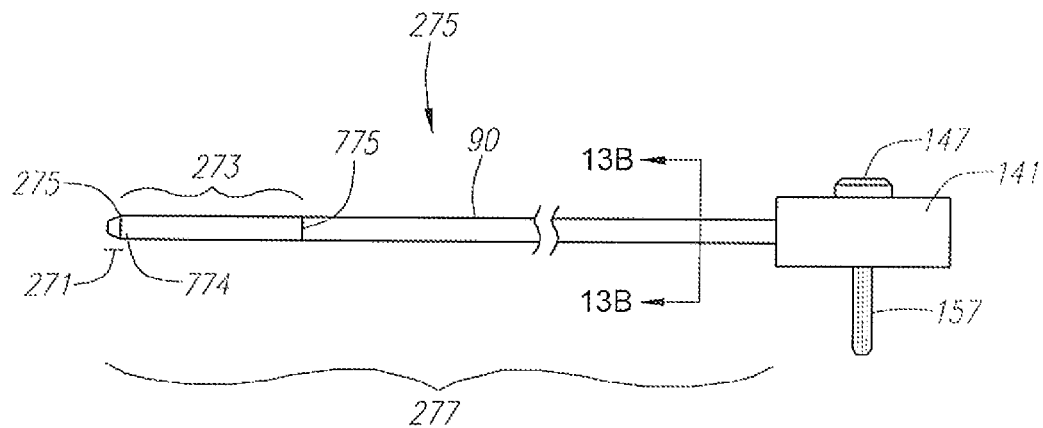
FIGS. 13A-B illustrate embodiments of a catheter instrument wherein localization sensors may be deployed at various positions.
Figure 13B:
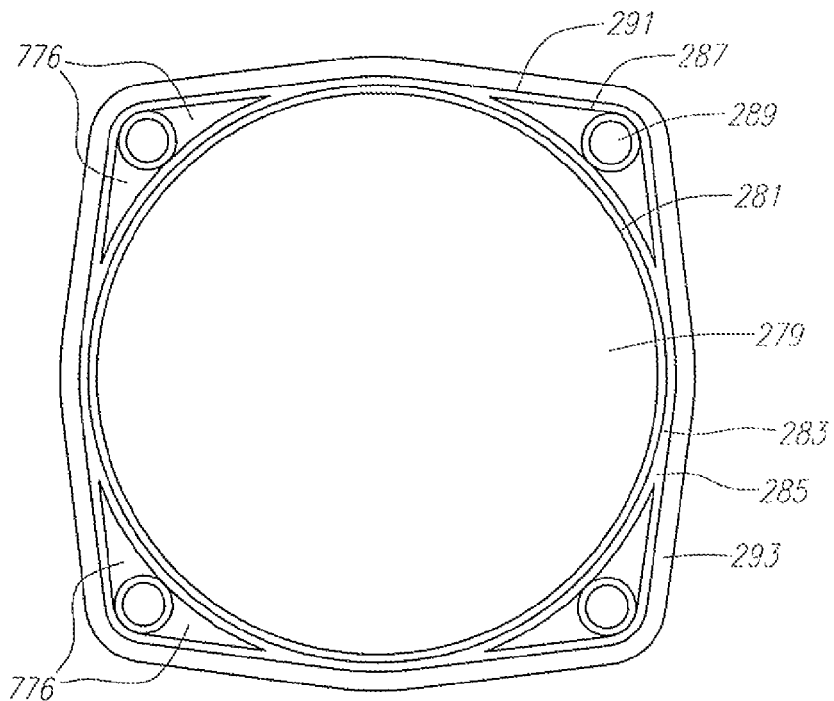
Figure 14:
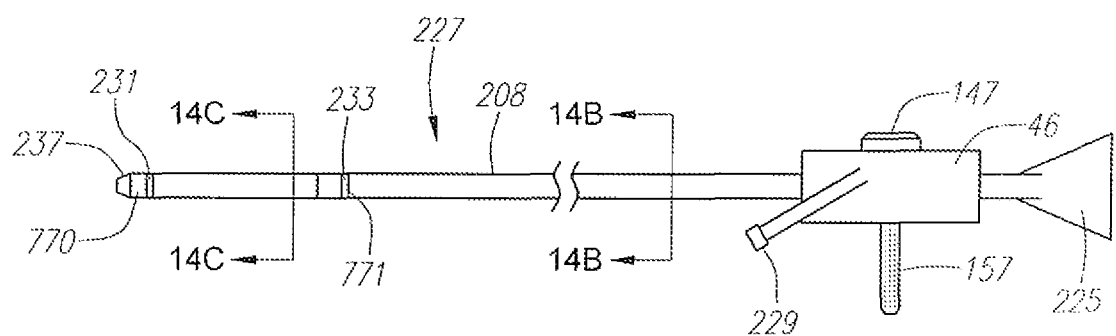
FIG. 14 illustrates embodiments of a catheter instrument wherein localization sensors may be deployed at various positions.

One way to increase instinctiveness of navigation of an instrument within, for example, a tissue structure, is to build a model utilizing an active instrument, such as a guide instrument coaxially associated with an ablation catheter, such that the model is inherently registered with the coordinate system of the active instrument. In one embodiment, a model of structures surrounding an instrument may be created using localization sensing at the distal tip of the instrument. For example, in one embodiment, a localization sensor, such as those available from the Biosense Webster division of Johnson & Johnson, Inc., Ascension Technologies, Inc., or the Endocardial Solutions division of St. Jude Medical, Inc., may be coupled to the distal tip of a guide instrument or other instrument, such as an ablation catheter, which itself is coupled to the distal tip of a guide or other instrument. One embodiment with many localizationsensors (52) is depicted in FIG. 12A. It may be desirable to provide at least one additional localization sensor (52) to help mitigate errors associated with absolute localization to an emitter (54) which may be, for example, under the operating table (56), and also for common mode rejection. Localization sensors (52) may be integrated, for example, as purchased off the shelf into the body of an instrument (e.g., embedded in a wall or in an internal space within the instrument), but may also be deconstructed (i.e., the individual coils) and oriented appropriately in an integrated fashion at the end of an instrument, or several locations therein, as will be appreciated by those skilled in the art. Wire leads provided to communicate current through the coils as result of magnetic flux may be integrated between polymer layers, braided layers, or almost any other layers of the instrument. For example, the leads may be woven into braided layers of the instrument body construction, and are preferably located in available void space (i.e., left from keying structures, etc) to minimize the requisite total instrument outer diameter. Metal structures, such as, e.g., braids and metal spines or kink resistors, may operate as Faraday cages and should be avoided when positioning the sensors on/in the instrument to maintain signal quality. FIGS. 13 and 14 depict various positions (770-776) for the localization sensors that may be desireable.

With movement of the distal tip of the instrument, and detection of contact with surrounding tissues utilizing, for example, impedance monitoring and/or electrophysiologic signal sensing, an inner surface map may be iteratively created from a series of saved surface points. In another embodiment, a model may be created without a localization sensor utilizing another mode of position determination, such as the kinematics and mechanics of the known instrument system. In other words, with, for example, electrophysiology signal sensing and/or impedance monitoring to determine contact, along with inverse kinematics to back out the position of the contact relative to the coordinate system of the instrument, a surface model may be iteratively created. Suitable contact sensors for such embodiments include those described above. For example, a mismatch between a) commanded instrument position based upon instrument and instrument driver kinematics and b) actual instrument position based upon fluoroscopy, ultrasound, localization, or other real or near-real time modality may be interpreted as an indication of contact or instrument fault (i.e., a broken steering tension member). Load cells configured to detect steering tension member tensions may also be utilized to determine that an instrument is in contact with surface other than free space. Proximally-positioned load cells may also be utilized to detect relative load between coaxial instrument members, or direct loads applied by distally adjacent surfaces upon the most distally-positioned instrument tip. Furthermore, strain gages may be utilized distally to detect contact and force, along with impedance monitoring. Ultrasound may also be utilized with localization sensing to create surface models.

Another way to increase instinctiveness of navigation of an instrument within, for example, a tissue structure, is to import, register, scale, and perhaps iteratively refine a surface model created preoperatively or interoperatively. In one embodiment, for example, CT or MR imaging may be utilized to capture a relatively precise image of a tissue structure, such as the heart. Gating may be utilized to capture various portions of the image sequentially during the same portion of the heart and/or breathing cycle. The portions may be assembled as a voxel three-dimensional image, and may be converted, for example, to a surface model (i.e., a triangular mesh) using segmentation software. Alternatively, portions of an image may be acquired as categorized by the time sequence in the heart cycle, reassembled as a voxel "movie" projected over time, and segmented into a three-dimensional surface model configured to move with time in accordance with the movement of the associated tissue during the image acquisition. Such surface models may be rendered as objects, and may be registered to the coordinate system of an instrument using algorithms configured to snap, rotate, and/or scale an object into position relative to other surrounding objects in three-dimensions based upon best fits to known anatomical locations. For example, an operator may drive an instrument to a known anatomical location using fluoroscopy, ultrasound, or other imaging modalities, then register the surface model to the other objects by establishing, for example, a least squares fit between the known anatomical locations and the same anatomical features found on the surface model).

Once the surface model is registered to the instrument and/or other objects, the operator may instinctively navigate the instrument adjacent the surface model, and may continue to refine and/or build out the surface model using techniques such as those described above (with or without utilizing localization sensors). Other (e.g., nearby) critical anatomy may also be included in the model of the subject tissue structure, to facilitate safe and controlled navigation. For example, it may be desirable in a left atrial ablation procedure to acquire, import, and register a surface model based not only upon structures of the left atrium, but also based upon structures of the entire heart and portion of the esophagus adjacent the left heart. Indeed, by utilizing localization sensors or other modalities of registering objects in three dimensions, many different types of images may be incorporated to bring to the operator's navigation experience the various strengths and weaknesses of such modalities, and the pertinent image objects may be highlighted or de-emphasized in accordance with these strengths and weaknesses.

Further, imported and registered images may be preoperatively acquired—or may be acquired during the interventional procedure. For example, when using an embodiment of a robotic catheter instrument to perform a cardiac ablation intervention, a gated CT voxel still image ("still shot") may be acquired preoperatively, along with a CT voxel "movie" of the heart moving throughout the heart cycle. Both of these voxel models may be converted to surface models with segmentation software. During the procedure, two or three dimensional ultrasound images may be registered to the imported and registered still shot CT surface model and/or the imported and registered movie CT surface model. A model of the tissue surfaces local to the subject instrument may also be created iteratively using contact sensing or other modalities, as described above. Once all of the objects are registered to each other and the coordinate system of the images relative to the distal tip of the instrument is known, for example using a localization sensor coupled to or embedded within the distal tip of the instrument (and, in one embodiment, at least one other localization sensor coupled to or embedded within a more proximal location of the distal tip of the instrument for common mode error mitigation), transforms between the various coordinate systems may be calculated utilizing conventional techniques, and the three dimensional relationships of the various objects made instinctive to the system operator.

Given the instinctive relationship of the objects and the ability, in one embodiment, to adjust the visual transparency of various selected objects, the operator may "dial up" or "dial down" the intensity of certain objects as appropriate. For example, if approaching the atrial septum from the inferior vena cava, the operator may wish to increase the intensity of an ICE ultrasound image relative to other objects, since the ICE image object may be particularly well suited for examining the septum and other adjacent tissue structures, e.g., for viewing a transseptal puncture and transseptal flow. Before executing a transseptal puncture, the operator may wish to increase the relative intensity or viewability of the still shot CT model, or bring in the movie CT model to observe the aortic outflow tract, dimensions of the left atrium, and possible structures to avoid, such as the adjacent esophagus, which may be displayed as a portion of either CT model. In another embodiment, the CT models may be highlighted to identify localized edema, a tumor, or other structures within a wall that may be otherwise difficult to see with fluoroscopy, optical imaging, ultrasound, or other images brought into the mix. Thus, a system operator may utilize multiple imaging and modeling modalities in a robust navigation and intervention scenario.

In various embodiments, localization sensors may be utilized to build models, register images, and generally navigate with known realtime or near-realtime position detection. Two embodiments of integration of localization systems into the subject robotic catheter system are now described in view of the discussion above. In one embodiment, as depicted, for example, in FIGS. 12A-B, a localization system, such as the Carto XP system by Biosense Webster, or the Ensite system by Endocardial Solutions, or a localization system by Ascension Technologies, Inc., may be configured to output location data (x, y, z coordinates) for each sensor, preferably along with orientation data (yaw, pitch, roll) for each sensor, and image "camera position" and/or orientation for images produced by the localization system. Sensor location and orientation, and camera orientation or position may be sent using a protocol such as TCPIP over an Ethernet connection at a frequency of, for example, between about 50 Hz and about 100 Hz, in the form of updated packets (for example, in a format like "beginning of packet . . . [bunch of numbers] . . . end of packet"). Images may be transferred to the displays of the robotic system using standard video cables. Thus, via TCPIP, the robotic system would receive a new packet every cycle containing location and orientation data which would be utilized by the robotic system for basic contact sensing as described above (i.e., a move is commanded, yet location data does not change) or fault detection (a move is commanded, yet location data does not change).

Indeed, true closed loop control (i.e., where the operator can interactively navigate to a desired location and know that he is getting there) is possible. Knowledge of the kinematics and mechanics of the instrument system may be combined with other available information from localization and/or other imaging modalities in a symbiotic relationship which may be known as "adaptive kinematics", wherein the sum control knowledge of the information coming from kinematics, imaging, contact sensing, etc., creates a better understanding of the system, and also of each subsystem. For example, if localization data indicates that a relatively stiff catheter is straining or stretching a much more significant amount that the known kinematics and/or mechanics of the catheter dictate should be the case, the localization data may be ignored or filtered appropriately for a more accurate understanding of where the sensor coupled to the instrument really is located or oriented.

Figure 12C:
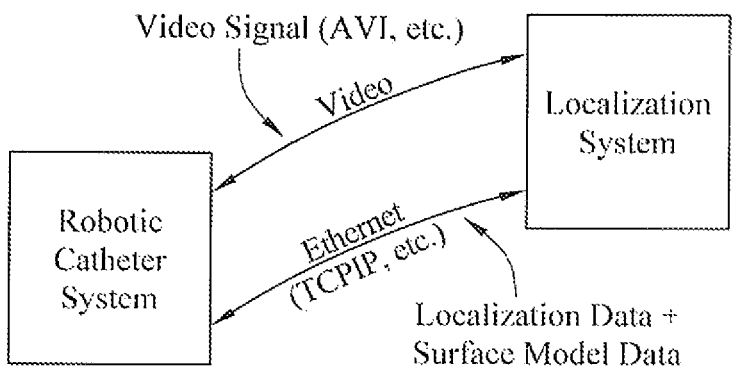
FIG. 12C is a block diagram illustrating another embodiment of a system wherein a surface model of one or more pertinent tissue structures is imported and registered.

In various embodiments, such as the one depicted, for example, in FIG. 12C, a surface model of one or more pertinent tissue structures is imported and registered—and with such registration and localization, utilized, for example, to: a) better understand the location and orientation of the distal tip of the subject instrument; b) provide haptic feedback regarding contact to surfaces; c) conduct "interpreted motion" as described above; d) conduct path and/or trajectory planning (preoperative, or offline intraoperatively); and e) provide "smart" automation functionality to the operator (for example, pick the best route to the selected points, use path/trajectory planning—and use the sensed position to follow that, make sure the operator knows that he is getting stuck on a surface, etc; indeed, points may be marked with master following mode offline—then the operator may select "execute" and observe the automation). Further, "reachability" analysis may be conducted with the "master following mode" offline to determine, for example, optimal sheath instrument location relative to guide instrument, and/or desirable position of a transseptal puncture to allow for desired reachability to key locations of the atrium.

Figure 12D:
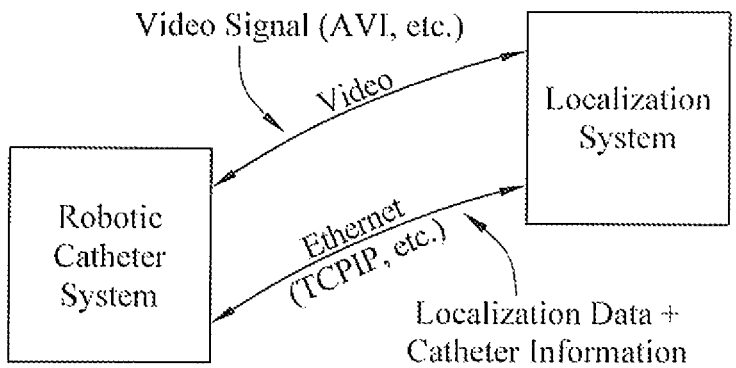
FIG. 12D is a block diagram illustrating another embodiment of a system wherein updated catheter information may be passed back to the localization system from the robotic catheter system.

Referring to FIG. 12D, in another embodiment, updated catheter (or more generically, "instrument") information may be passed back to the localization system, preferably via a fast network and protocol, such as TCP/IP, to provide the localization system with information sufficient to present a depiction of the commanded catheter position upon the localization system display in the frame of reference of the localization system. As per the discussion above, various catheter or instrument system embodiments may comprise multiple instruments. For example, in one embodiment, an ablation catheter may be positioned within a lumen of a robotically steerable guide instrument, which may be positioned within a lumen of a robotically steerable sheath instrument. In other embodiments, systems may comprise more, or less, integrated hardware componentry. Information regarding a single, or multiple catheters or instruments may be utilized as described herein to provide the operator with high levels of controllability while operating steerable instrument systems as well as localization systems.

In one embodiment, the catheter information comprises an updated complete surface model, such as a triangular mesh of the distal portion of the subject instrument, in the localization system frame of reference. In such embodiment, the surface model may be brought in as an object and depicted in 3-D space relative to other depicted structures or instruments. For example, the commanded catheter position surface model may be depicted in a different transparency or color than an "actual" position surface model, as determined by a localization system, which may also be depicted as an object within the display of the localization system. As described above, differences in the position and orientation of various aspects of the commanded versus actual catheter tip objects may be interpreted as contact with a structure, errors in the control or mechanical systems, etc. To prevent direct overlapping of the "actual" and commanded objects on the display for better operator comparison, an offset may be selected to move the two objects on the display a given distance from each other. Colors and transparencies may also be adjusted to provide an operator with better comparability during overlap scenarios, or in scenarios with desired offsetting.

In another embodiment, the catheter information comprises an updated list of points representative of the commanded instrument surface model in the localization system frame of reference. Such points may be utilized by the localization system to build and display a surface model, such as a triangular mesh, of the commanded catheter position. Once built, each updated model may be utilized as described above in reference to the embodiment wherein the model itself is transferred from the robotic catheter system to the localization system. Transferring updated discrete sets of points is relatively efficient in terms of data transfer, in comparison to transferring a surface model, and the processing to build a surface model from the points may be distributed to other computing resources on the localization system.

In another embodiment, an updated kinematic model of each instrument, as well as updated coordinates for tip position in the localization system frame of reference, may be passed back to the localization system, to enable the localization system to build points and/or a surface model of the commanded catheter position for display as an object on the localization system display relative to other pertinent objects. In one embodiment, the kinematic models of the instruments change less often than the tip locations of the instruments, and thus a more streamlined packet of only tip locations may be passed to the localization system to generate an updated commanded catheter model, as opposed to a more robust packet containing both updated kinematic models and updated instrument tip locations. For example, in one embodiment, the kinematics of an instrument may be similar in one three-dimensional envelope space, but may change to a more or less linear kinematic relationship outside of that envelope. In such an embodiment, while the instrument is in the first space, a first kinematic model may be passed to, or triggered from memory within, the localization system, and subsequent updates of catheter information while the instrument is in such first space may comprise merely tip position information. Further, in such embodiment, when the instrument is moved outside of the first envelope space, a second kinematic model may be passed to, or triggered from memory within, the localization, and subsequent updates of catheter information while the instrument is in the second space may comprise merely tip position information. In another embodiment, instrument pointer locations other than or in addition to the tip locations may be passed to provide more refined inputs for the pertinent kinematic models of the instruments.

To ensure that the catheter information is passed to the localization system in the localization system frame of reference, some up-front coordination of the robotic catheter system frame of reference and localization system frame of reference may be employed. In one embodiment, the two coordinate systems may be coordinated fairly simply by knowing in each system where the catheter (or more generically "instrument") and image camera-eye view is with respect to the "world" coordinate system (that is, knowing position and orientation of each). With this information, simple transformations may be utilized to understand the positions of the catheter and image camera in both frames of reference, and to enable seamless passing of data regarding position and orientation from one system to the other, as depicted in FIG. 12D.

Given a relative position of a sheath instrument in a body, and known kinematic relationships of the instrument system, in certain embodiments it is desirable to run software algorhythms to determine a "reachability" of potential destination points of interest to the system operator. By way of example, using a triangular heart mesh model, the system may analyze the reachability of the vertex point of every triangle on the model. The "reachability" may be expressed as a "yes" or "no," or as a scaled gradation, for example, with location zones having a green/yellow/red coloring scheme applied on a display to indicate the degree of reachability of each zone (e.g., green=reachable within normal system constraints; yellow=reachable only with special maneuvers; red=not reachable from the present location without re-positioning the instrument). The system operator can view the reachability of desired locations from the present position of the instrument, move the instrument, and then reanalyze the reachability of the desired locations from the new instrument position.

Preferably, the reachability analysis will take into account the likelihood that the instrument will get hung up into tissue or some other structure in trying to navigate from the present to a desired location. If a location or point can be reached, reachability analysis may be utilized to determine, for example, whether the body of the instrument proximal to the distal tip may become hung up into tissue or some other nearby structure. In one embodiment, the instrument body may be analyzed as a series of segments, with collision detection algorithms being run for each discrete portion of the instrument body (as positioned by the desired tip location and kinematics/mechanics) and the tissue structure mesh.

In such embodiment, if a collision is required for the instrument to reach a desired endpoint given the analysis of the segments, the location of such desired endpoint may be assigned a color designated to have a certain meaning to the operator. For example, if a collision is not required and there is no navigational challenge, a green graphical user interface color may be assigned to such segment—meaning that the operator may navigate the instrument to that point without colliding with nearby structures; a pink color assignment may be utilized to mean that the desired maneuver is possible but in the current position of the instrument or instruments (for example, coaxially-interfaced guide and sheath instruments with another instrument positioned within a working lumen of the guide instrument) at least a portion thereof would collide with or deflect the adjacent tissue structure in order for the distal tip to be located at the desired endpoint; a red color assignment on the graphical user interface may be utilized in such a configuration to provide feedback to the operator that the desired endpoint is not reachable with the current instrument configuration. Thus, for a given instrument configuration and a subject tissue structure, the operator may use reachability analysis to understand what is reachable easily, reachable with some repositioning of instrumentation, or not reachable. As described above, in other embodiments, "reachability" may be expressed to the operator as a "yes" or "no", a scale of numerals, or other scaled gradation.

In another embodiment, individual segments may be assigned colors pertinent to their particular impending collision status with nearby structures should a planned move be executed.

In another embodiment, logic pertinent to the known kinematics of the given instrument may be interjected into the reachability analysis to an even further degree, such that sub-gradations of reachability are depicted for the operator, which are associated with the ease of reachability given the instrument performance. For example, relating to the embodiment described above, if a desired endpoint in the example above would be assigned a green user interface color, kinematic logic regarding the instrument may be interjected to assign a dark green, for example, if the desired endpoint is reachable very easily without taking any of the instrument drive motors or tension elements past a preseleted load or defection envelope or threshold; the desired endpoint may be assigned a light green color, for example, if the drive motors or tension elements need to exceed a preselected envelope or threshold.

In one embodiment, reachability analysis may be conducted offline (utilizing the computing systems of the subject robotic catheter system, but without an associated instrument or instrument driver attached; rather, a simulated instrument driver and instrument set may be utilized within the computer software)—perhaps before an operative procedure—for planning, training, interoperative time saving, or other reasons. For example, it is highly desirable in one embodiment to utilized preoperatively acquired image data (from CT, MR, radiography, and/or ultrasound, for example) along with reachability analysis to preoperatively simulate navigating the planned instrumentation configuration to all of the desired endpoints, choose interventional locations, such as transseptal crossing location, to maximize efficiency and safety during the subsequent procedure. Such a configuration may be utilized for training and/or collaboration with different users in other embodiments. Alternatively, interoperatively, an operator may wish to decouple master following and conduct a brief session of reachability analysis before switching back to master following mode—with the purpose, for example, of trying to use the simulation capabilities of reachability analysis to plot a next move—rather than doing so experimentally with the instrumentation in the patient.

In another embodiment, pre-set logic may be blended into the reachability analysis or simulation to assist the operator in planning to avoid key sensitive structures. For example, the software may be configured to automatically identify, and/or have the operator identify, structures such as the aortic outflow tract of the heart in the preoperative or intraoperative image data; the system may then be configured to assist the operator in avoiding collisions between such structure and any of the pertinent instrumentation given planned endpoints, paths, and/or trajectories. In another variation, such analysis may be utilized to assist the operator in affirmatively reaching and/or intervening with particular structures (for example, the system may be configured to assist the operator in reaching and safely crossing the atrial septum with a safe and desirable trajectory and displacement, and may be configured to select a portion of such atrial septum for crossing given the plans of the operator for using the instrument set in the left atrium subsequent to crossing such septum, as well as logical factors such as key structures to avoid when crossing such septum).

The forgoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims.

What is claimed is:

1. A robotic instrument system, comprising:
   an elongate instrument;
   a controller configured to selectively actuate one or more motors operatively coupled to the instrument to thereby selectively move a distal end portion of the instrument,
   wherein the controller is further configured to determine a reach of the instrument distal end portion within an anatomical workspace in which the instrument is located, based at least in part upon a present relative position of the instrument distal end portion,
   wherein the controller is further configured to determine, based on the determined reach, a plurality of location zones and a reachability of each of the location zones,
   wherein the reachability of each of the location zones is displayed in a manner that indicates which areas of the workspace may be reached by the instrument distal end portion from the present position of the instrument, and which areas cannot be reached by the instrument distal end portion from the present position of the instrument; and
   a display in communication with the controller, wherein the controller causes the plurality of location zones and the reachability of each of the location zones to be indicated on the display,
   wherein the plurality of location zones include a first location zone highlighted on the display to indicate that the first location zone can be reached by the instrument distal end portion from the present position of the instrument by normal maneuvering, a second location zone highlighted on the display to indicate the second location zone may possibly be reached by the instrument distal end portion from the present position of the instrument by using additional or special maneuvering, and a third location zone highlighted on the display to indicate that the third location zone cannot be reached by the instrument distal end portion from the present position of the instrument.

2. The system of claim 1, wherein the controller determines the reach of the instrument distal end portion further based at least in part on a kinematic model of the instrument.

3. The system of claim 1, wherein the reachability of each of the location zones is displayed as a "yes" or "no", or as a numeric or other scaled gradation.

4. The system of claim 1, wherein in determining the reach of the instrument distal end portion, the controller determines and causes to be displayed a relative instrument performance in reaching respective locations and positions in the workspace.

5. The system of claim 1, wherein in determining the reach of the instrument distal end portion, the controller takes into account one or more of locations of sensitive tissue structures in the workspace to be avoided, locations of target tissue structures in the workspace to be reached, planned trajectories of the instrument distal end portion, and planned end points of the instrument distal end portion.

6. The system of claim 1, wherein the controller displays the determined reach of the instrument distal end portion overlaying an image of the anatomic workspace.

7. The system of claim 6, wherein the image of the anatomic workspace is obtained from a model of the workspace, from an imaging system, or both.

8. The system of claim 6, wherein the displayed reach of the instrument distal end portion includes an image of the instrument distal end portion obtained from a model of the instrument, from an imaging system, or both.

9. The system of claim 1, wherein the controller determines the reach of the instrument distal end portion further based at least in part on a likelihood that some portion of the instrument will get hung up into tissue or some other structure in an attempted move from its present position to other potential locations and positions in the anatomical workspace.

10. The system of claim 9, wherein the portion of the instrument is proximal to its distal tip, and wherein the controller analyzes the instrument as a series of segments, with collision detection algorithms being run for each discrete segment of the instrument.

11. The system of claim 10, wherein the individual instrument segments are displayed with assigned colors representing their respective impending collision status with nearby structures.

12. The system of claim 10, wherein if a collision is required for the instrument distal end portion to reach a particular position or range of positions in the anatomical workspace when moved from its present position, the location of each such position is highlighted or otherwise designated on the display.

13. A robotic instrument system, comprising:
an elongate flexible instrument;
a display; and
a controller in communication with the display and configured to selectively actuate one or more motors operatively coupled to the instrument to thereby selectively move a distal end portion of the instrument, wherein the controller is further configured to determine a reach of the instrument distal end portion within an anatomical workspace in which the instrument is located, based on a present relative position of the instrument distal end portion, a kinematic model of the instrument, and one or more of
a likelihood that some portion of the instrument will get hung up into tissue or some other structure in an attempted move from its present position to other potential locations and positions in the anatomical workspace,
a relative ease or difficulty in reaching respective locations and positions in the workspace,
a relative instrument performance in reaching respective locations and positions in the workspace, locations of sensitive tissue structures in the workspace to be avoided,
locations of target tissue structures in the workspace to be reached,
planned trajectories of the instrument distal end portion, and
planned end points of the instrument distal end portion,
wherein the controller is further configured to determine, based on the determined reach, a plurality of location zones and a reachability of each of the location zones,
wherein the controller causes the plurality of location zones and the reachability of each of the location zones to be indicated on the display, the reachability of each of the location zones being displayed in a manner that indicates which areas of the workspace may be reached by the instrument distal end portion from the present position of the instrument, and which areas cannot be reached by the instrument distal end portion from the present position of the instrument; and
wherein the plurality of location zones include a first location zone highlighted on the display to indicate that the first location zone can be reached by the instrument distal end portion from the present position of the instrument by normal maneuvering, a second location zone highlighted on the display to indicate the second location zone may possibly be reached by the instrument distal end portion from the present position of the instrument by using additional or special maneuvering, and a third location zone highlighted on the display to indicate that the third location zone cannot be reached by the instrument distal end portion from the present position of the instrument.

14. The system of claim 13, wherein the controller is configured to display the determined reach of the instrument distal end portion on the display, overlaying an image of the anatomic workspace, wherein the image of the anatomic workspace is obtained from a model of the workspace, from an imaging system, or both.

15. The system of claim 14, wherein the displayed reach of the instrument distal end portion includes an image of the instrument distal end portion obtained from a model of the instrument, from an imaging system, or both.

16. The system of claim 14, wherein if a collision is required for the instrument distal end portion to reach a particular position or range of positions in the anatomical workspace when moved from its present position, the location of each such position is highlighted or otherwise designated on the display.

* * * * *